United States Patent
Yamaya

(10) Patent No.: US 12,279,750 B2
(45) Date of Patent: Apr. 22, 2025

(54) ENDOSCOPE HAVING COVER COVERING SPOOL ADHESION PORTION AND METHOD FOR MANUFACTURING ENDOSCOPE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 678 days.

(21) Appl. No.: 17/459,453

(22) Filed: Aug. 27, 2021

(65) Prior Publication Data
US 2021/0386272 A1   Dec. 16, 2021

Related U.S. Application Data

(63) Continuation of application No. PCT/JP2019/009739, filed on Mar. 11, 2019.

(51) Int. Cl.
*A61B 1/00* (2006.01)
*A61B 1/005* (2006.01)

(52) U.S. Cl.
CPC .......... *A61B 1/0011* (2013.01); *A61B 1/0008* (2013.01); *A61B 1/0051* (2013.01)

(58) Field of Classification Search
CPC ... A61B 1/0011; A61B 1/0051; A61B 1/0014; A61B 1/00137; A61B 1/0008; A61B 1/00135; A61B 1/00133
See application file for complete search history.

(56) References Cited

U.S. PATENT DOCUMENTS

| | | | | |
|---|---|---|---|---|
| 4,347,837 A | * | 9/1982 | Hosono | G02B 23/2476 356/241.4 |
| 4,805,596 A | * | 2/1989 | Hatori | A61B 1/0057 600/142 |

(Continued)

FOREIGN PATENT DOCUMENTS

| CN | 102595997 A | 7/2012 |
|---|---|---|
| CN | 204328300 U | 5/2015 |

(Continued)

OTHER PUBLICATIONS

International Search Report dated Jun. 11, 2019 received in PCT/JP2019/009739.

*Primary Examiner* — John P Leubecker
*Assistant Examiner* — Li-Ting Song
(74) *Attorney, Agent, or Firm* — Scully, Scott, Murphy & Presser, P.C.

(57) ABSTRACT

An endoscope includes: an envelope provided so as to cover an outer surface of an insertion portion; a filamentous member that is wound around an outer surface of the envelope and causes an end portion of the envelope to be fixed to the insertion portion; a resin applied to a spool member in which the filamentous member is wound around the envelope; a protruding portion provided on the outer surface of the insertion portion and formed in one part of the insertion portion in a circumferential direction; a cover member mounted so as to cover an outer circumference of the resin; and a concave portion provided in an inner circumferential surface of the cover member, including a cross-sectional shape homothetic to a cross-sectional shape of the protruding portion, and disposed in a position shifted from the protruding portion in a circumferential direction of the insertion portion.

20 Claims, 27 Drawing Sheets

(56) References Cited

U.S. PATENT DOCUMENTS

| | | | | |
|---|---|---|---|---|
| 4,807,598 | A | * | 2/1989 | Hasegawa .......... A61B 1/00071 600/153 |
| 5,591,120 | A | * | 1/1997 | Machida .............. A61B 1/0011 600/920 |
| 6,514,198 | B2 | * | 2/2003 | Ishibiki .............. A61B 1/00071 600/131 |
| 7,822,154 | B2 | * | 10/2010 | Chen .................. H04B 7/18515 702/69 |
| 8,226,547 | B2 | * | 7/2012 | Tsutsumi ............... A61B 1/005 600/129 |
| 8,790,249 | B2 | * | 7/2014 | Tanoue .............. G02B 23/2484 600/129 |
| 9,661,993 | B2 | * | 5/2017 | Sakata ................. A61B 1/0055 |
| 9,822,287 | B2 | * | 11/2017 | Yokoyama ............. A61B 1/051 |
| 11,284,780 | B2 | * | 3/2022 | Niino ...................... A61B 1/005 |
| 2007/0167674 | A1 | * | 7/2007 | Toyama ............. A61B 1/00071 600/101 |
| 2008/0154094 | A1 | * | 6/2008 | Nakamura ............. A61B 1/005 600/129 |
| 2008/0294007 | A1 | | 11/2008 | Takada |
| 2009/0093679 | A1 | | 4/2009 | Suigetsu et al. |
| 2011/0049040 | A1 | | 3/2011 | Mark |
| 2011/0230717 | A1 | * | 9/2011 | Konstorum .......... A61B 1/0011 156/86 |
| 2012/0215068 | A1 | * | 8/2012 | Furuta .................. A61B 1/0051 600/125 |
| 2013/0035549 | A1 | * | 2/2013 | Abe ................... A61B 1/00078 600/121 |
| 2013/0050457 | A1 | * | 2/2013 | Murayama ......... A61B 1/00124 348/75 |
| 2013/0217963 | A1 | * | 8/2013 | Naito ....................... A61B 1/05 600/104 |
| 2016/0367110 | A1 | * | 12/2016 | Tanii ...................... A61B 1/015 |
| 2017/0086655 | A1 | | 3/2017 | Fujimoto |
| 2017/0231476 | A1 | * | 8/2017 | Matsuo .............. G02B 23/2476 600/104 |
| 2020/0178779 | A1 | * | 6/2020 | Komoro ................... A61B 1/05 |
| 2021/0212556 | A1 | * | 7/2021 | Nguyen ............. A61B 1/00128 |
| 2023/0100410 | A1 | * | 3/2023 | Yamamoto ........... A61B 1/0055 600/140 |
| 2024/0206710 | A1 | * | 6/2024 | Sato ....................... A61B 1/018 |

FOREIGN PATENT DOCUMENTS

| | | | |
|---|---|---|---|
| EP | 1 920 707 | A1 | 5/2008 |
| EP | 3 143 923 | A1 | 3/2017 |
| JP | H09-236588 | A | 9/1997 |
| JP | H11-253388 | A | 9/1999 |
| JP | 2000041937 | A * | 2/2000 |
| JP | 2001340457 | A | 12/2001 |
| JP | 3360452 | B2 | 12/2002 |
| JP | 2008-017875 | A | 1/2008 |
| JP | 2008-136847 | A | 6/2008 |
| JP | 2008-259634 | A | 10/2008 |
| JP | 2013244266 | A * | 12/2013 |
| JP | 2017217250 | A * | 12/2017 |
| JP | 2018-105992 | A | 7/2018 |
| WO | 2008/126727 | A1 | 10/2008 |
| WO | 2009/101386 | A1 | 8/2009 |
| WO | 2011/052303 | A1 | 5/2011 |
| WO | 2016/103817 | A1 | 6/2016 |

* cited by examiner

ENDOSCOPE HAVING COVER COVERING SPOOL ADHESION PORTION AND METHOD FOR MANUFACTURING ENDOSCOPE

CROSS REFERENCE TO RELATED APPLICATION

This application is a continuation application of PCT/JP2019/009739 filed on Mar. 11, 2019, the entire contents of which are incorporated herein by this reference.

BACKGROUND OF THE INVENTION

1. Field of the Invention

The present invention relates to an endoscope including an insertion portion configured to be inserted into a subject and particularly including a bending portion provided in the insertion portion, and a method for manufacturing the endoscope.

2. Description of the Related Art

As it is well known, endoscopes are widely used for observation, treatment, and the like of an inside of a body (an inside of a body cavity) of a living body or inspection, repairing, and the like of an inside of a plant facility for industrial use. Endoscopes as above includes an insertion portion to be inserted into a body cavity that bends and a pipeline. As the insertion portion of the endoscope, an insertion portion including a bending portion that is provided to be continuous with a proximal end side of a distal end portion and able to change a direction of the distal end portion is known.

For example, in International Publication No. WO 2011/052303, a fixing structure of an endoscope bending-portion envelope that prevents a spool adhesion portion that bonds a distal end portion and a bending-portion envelope to each other from deteriorating due to medicinal solution and the like at the time of cleaning and sterilization is disclosed.

The related-art endoscope as above has a configuration in which a ring-shaped member is fixed so as to cover an outer circumference of the spool adhesion portion before an adhesive agent of the spool adhesion portion hardens when both end portions of the bending envelope are fixed to the distal end portion and a flexible tube portion.

SUMMARY OF THE INVENTION

An endoscope in one aspect of the present invention includes: an insertion portion configured to be inserted into a subject; an envelope provided so as to cover an outer surface of the insertion portion; a filamentous member that is wound around an outer surface of the envelope and causes an end portion of the envelope to be fixed to the insertion portion; a resin applied to a spool member in which the filamentous member is wound around the envelope; a protrusion provided on the outer surface of the insertion portion and formed in one part of the insertion portion in a circumferential direction; a cover member mounted so as to cover an outer circumference of the resin; and a concave portion provided in an inner circumferential surface of the cover member, including a cross-sectional shape homothetic to a cross-sectional shape of the protrusion, and disposed in a position shifted from the protrusion in a circumferential direction of the insertion portion.

An endoscope in another aspect of the present invention includes: an insertion portion configured to be inserted into a subject; an envelope provided so as to cover an outer surface of the insertion portion; a filamentous member that is wound around an outer surface of the envelope and causes an end portion of the envelope to be fixed to the insertion portion; a resin applied to a spool member in which the filamentous member is wound around the envelope; a concave portion provided in the outer surface of the insertion portion and formed in one part of the insertion portion in a circumferential direction, the one part of the insertion portion in the circumferential direction being narrower than another part in a radial direction of the insertion portion; a cover member mounted so as to cover an outer circumference of the resin; and a protrusion provided so as to protrude from an inner circumferential surface of the cover member, including a cross-sectional shape homothetic to a cross-sectional shape of the concave portion, and disposed in a position shifted from the concave portion in the circumferential direction of the insertion portion.

A method for manufacturing an endoscope in one aspect of the present invention includes: providing an envelope such that the envelope covers an outer surface of an insertion portion configured to be inserted into a subject; winding a filamentous member around an outer surface of an end portion of the envelope and causing the end portion of the envelope to be fixed to the insertion portion; applying a resin to the filamentous member wound around the envelope; mounting a cover member in which a concave portion through which a protrusion formed on one part of the outer surface of the insertion portion is passable is formed such that an outer circumference of the resin is covered; causing the cover member to be rotated at predetermined angle to a position shifted from the protrusion in a circumferential direction of the insertion portion and placing the cover member in a state of being sandwiched between the envelope and the protrusion; and wiping off the resin that oozes out from an end portion of the cover member.

DETAILED DESCRIPTION OF THE PREFERRED EMBODIMENTS

An endoscope of one aspect of the present invention is described below with reference to the drawings. Note that in the description below, the drawings based on each embodiment are schematic drawings, and the relationship between the thickness and the width of each part, the ratio of the thicknesses of each part, and the like are different from actual relationships, ratios, and the like, and parts of which ratios and relationships of dimensions also differ throughout the drawings may be included.

First, the endoscope of one aspect of the present invention is described with reference to the drawings.

As the endoscope in a configuration description below, a so-called flexible scope including a flexible insertion portion so as to be inserted into body cavities of a living body, such as bronchi, urinary organs, from a gullet to a stomach, a small intestine, and a large intestine, is exemplified, but the endoscope can also be applied to a so-called rigid endoscope used in surgery in which an insertion portion having a bending portion is hard.

First Embodiment

Figure 1:
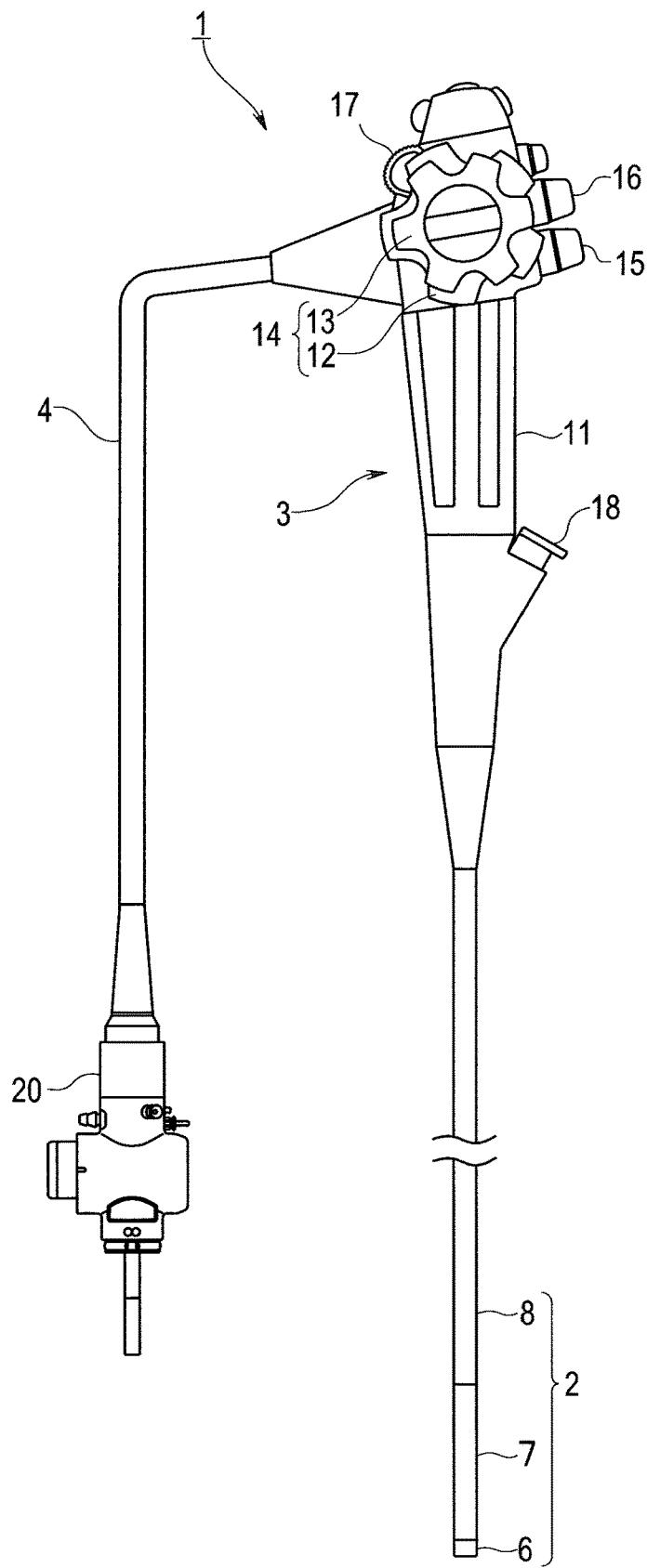
FIG. 1 is a view illustrating an exterior of an endoscope of a first embodiment of the present invention.

As illustrated in FIG. 1, an endoscope 1 of the embodiment is configured by including a long elongated insertion portion 2 that is inserted into a subject, an operation portion 3, and a universal cable 4 that is composite cable. The insertion portion 2 of the endoscope 1 is configured by including a distal end portion 6, a bending portion 7, and a flexible tube portion 8 in this order from a distal end.

In the operation portion 3, a bending operation knob 14 for performing bending operation of the bending portion 7 of the insertion portion 2 is turnably arranged, and an air/water feeding button 15, a suction button 16, a focus adjustment lever 17, and the like are provided.

In the bending operation knob 14, two substantially disk-shaped rotation knobs, that is, a UD bending operation knob 12 for performing the bending operation of the bending portion 7 in an up-down direction and an RL bending operation knob 13 for performing the bending operation of the bending portion 7 in a left-right direction are arranged in an overlapping manner.

A coupling portion between the insertion portion 2 and the operation portion 3 is configured by including a grasping portion 11 configured to be grasped by a user, and a treatment-instrument-insertion-channel insertion portion 18 that is disposed on the grasping portion 11 and serves as an opening portion of a treatment instrument insertion channel for allowing insertion of various treatment instruments arranged in the insertion portion 2.

The universal cable 4 extended from the operation portion 3 includes, at an extending end thereof, an endoscope connector 20 that is attachable to and removable from a light source apparatus that is not shown. The endoscope 1 of the embodiment transmits illumination light to the distal end portion 6 from the light source apparatus (not shown) by a light guide bundle (not shown) of illumination means arranged in the insertion portion 2, the operation portion 3, and the universal cable 4 in an inserted manner.

Although not shown here, coil-form coil cable is connected to the endoscope connector 20, and an electrical connector that is attachable to and removable from a video processor (not shown) is provided at an extending end of the coil cable.

Next, a configuration of the distal end part of the insertion portion 2 of the endoscope 1 of the embodiment is described below with reference to FIG. 2 and FIG. 3. In the description below, descriptions of well-known configurations of the insertion portion 2 are omitted.

Figure 2:
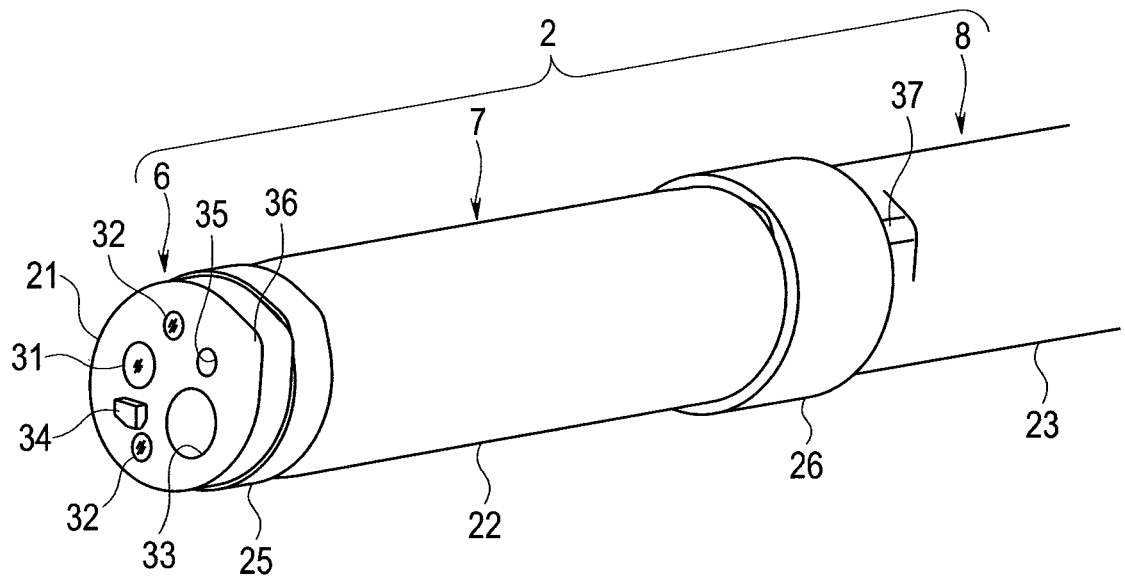
FIG. 2 is a perspective view illustrating a configuration of a distal end portion of an insertion portion of the first embodiment.
Figure 3:
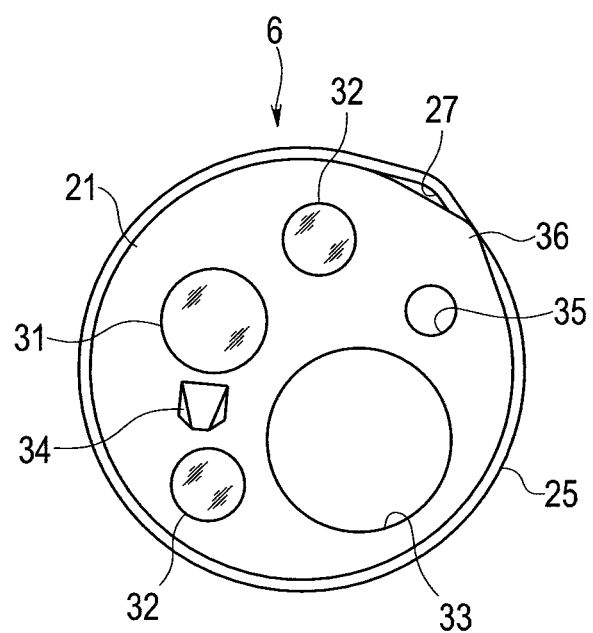
FIG. 3 is a front view illustrating a configuration of the distal end portion of the first embodiment.

As illustrated in FIG. 2 and FIG. 3, in the insertion portion 2 of the endoscope 1, on the distal end portion 6, a distal end cap 21 is provided on a distal end frame member 24 (see FIG. 7 and the like) that is not shown here but will be described below. In a distal end surface of the distal end cap 21, an observation window 31, two illumination windows 32, and an opening portion 33 of a channel that allows insertion of a treatment instrument and the like are provided.

On the distal end surface of the distal end cap 21, an air/water feeding nozzle 34 that spouts out fluid such as air and water onto a surface of the observation window 31 is provided, and an opening portion 35 of a forward water feeding channel that spouts out liquid such as normal saline to an object to be examined in front of the opening portion 35 is provided.

The distal end cap 21 includes, on one part of an outer circumferential portion thereof, a restricting convex portion 36 that protrudes outward. The distal end portion 6 may have a configuration in which the distal end cap 21 is not provided and the distal end frame member configures an outer surface.

The circumference of the bending portion 7 is covered with a bending portion skin 22. The bending portion skin 22 is formed in a cylindrical shape with a material such as rubber and resin and serves as an envelope that has flexibility and separates the bending portion 7 from an outside in a watertight manner. The flexible tube portion 8 is covered with an envelope 23. A restricting convex portion 37 that protrudes outward is provided on one part of a distal end outer circumference of the envelope 23.

In the bending portion 7, both ends of the bending portion skin 22 are fixed to the distal end portion 6 and the flexible tube portion 8 by spool adhesion portions 40 (shown in FIG. 7 and thereafter) that are not shown here but will be described below. A distal-end-side cover member 25 and a proximal-end-side cover member 26 that are annular ring members that are each about 0.2 mm to about 0.3 mm and cover the spool adhesion portions 40 on both of the ends of the bending portion skin 22 are provided.

Each of the distal-end-side cover member 25 and the proximal-end-side cover member 26 is provided so as to protect the spool adhesion portions 40 by covering the spool adhesion portions 40, and prevent deterioration of an adhesive agent due to medicinal solution used when the endoscope 1 is cleaned and sterilized.

Figure 4:
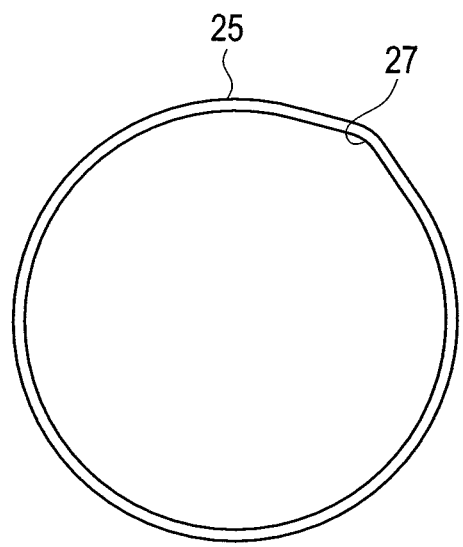
FIG. 4 is a plan view illustrating a configuration of a distal-end-side cover member of the first embodiment.

The distal-end-side cover member 25 is an annular member formed by metal such as stainless steel or hard resin such as polysulfone. As illustrated in FIG. 4, in the distal-end-side cover member 25, one part of an outer circumferential portion is formed in a protruding manner such that the diameter expands in an outer circumferential direction, and a restricting concave portion 27 is formed on an inner circumferential surface side of the protruding part.

The restricting concave portion 27 has a concave shape cross-sectional shape of which is homothetic to a cross-sectional shape of the restricting convex portion 36 formed on the distal end cap 21 of the distal end portion 6. It has been described that the restricting concave portion 27 has a concave shape cross-sectional shape of which is homothetic to the cross-sectional shape of the restricting convex portion 36 formed on the envelope 23 of the flexible tube portion 8, but the concave portion homothetic to the protrusion (restricting convex portion) is not limited to a concave portion having the same shape as the protrusion as long as the concave portion has a shape which is close to the protrusion and through which the protrusion may be caused to pass.

Figure 5:
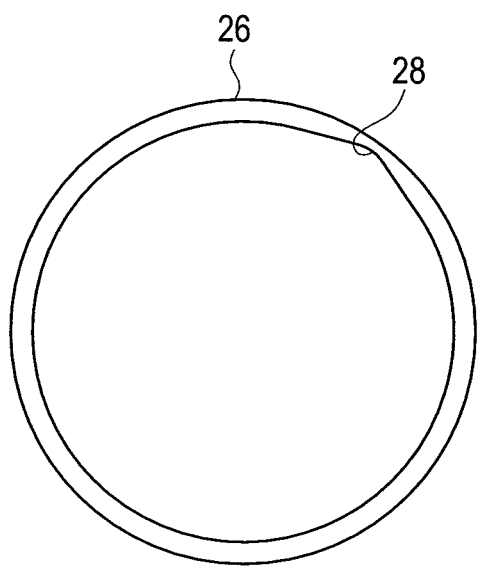
FIG. 5 is a plan view illustrating a configuration of a proximal-end-side cover member of the first embodiment.

The proximal-end-side cover member 26 is also an annular member formed by metal such as stainless steel or hard resin such as polysulfone. As illustrated in FIG. 5, in the proximal-end-side cover member 26, a restricting concave portion 28 is formed in one part of an inner circumferential surface.

The restricting concave portion 28 has a concave shape cross-sectional shape of which is homothetic to a cross-sectional shape of the restricting convex portion 37 formed on the envelope 23 of the flexible tube portion 8. It has been described that the restricting concave portion 28 has a concave shape cross-sectional shape of which is homothetic to the cross-sectional shape of the restricting convex portion 37 formed on the envelope 23 of the flexible tube portion 8, but the concave portion homothetic to the protrusion (restricting convex portion) is not limited to a concave portion having the same shape as the protrusion as long as the concave portion has a shape which is homothetic to the protrusion and through which the protrusion may be caused to pass.

Figure 6:
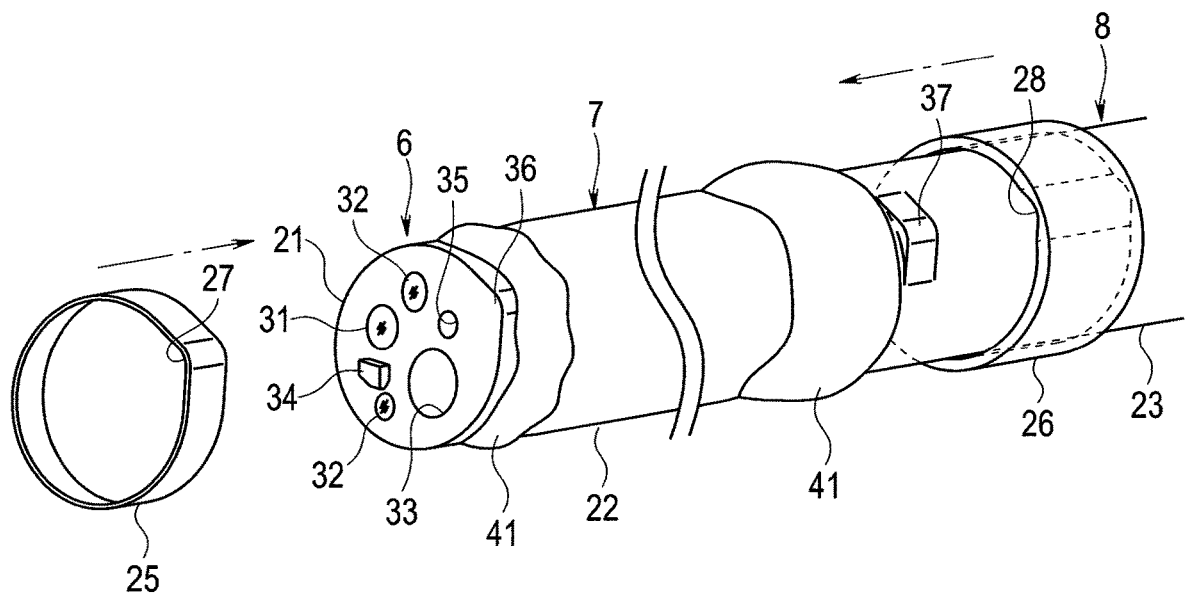
FIG. 6 is a perspective view illustrating a configuration of the distal end portion of the insertion portion of the first embodiment on which the cover members are to be mounted.
Figure 7:
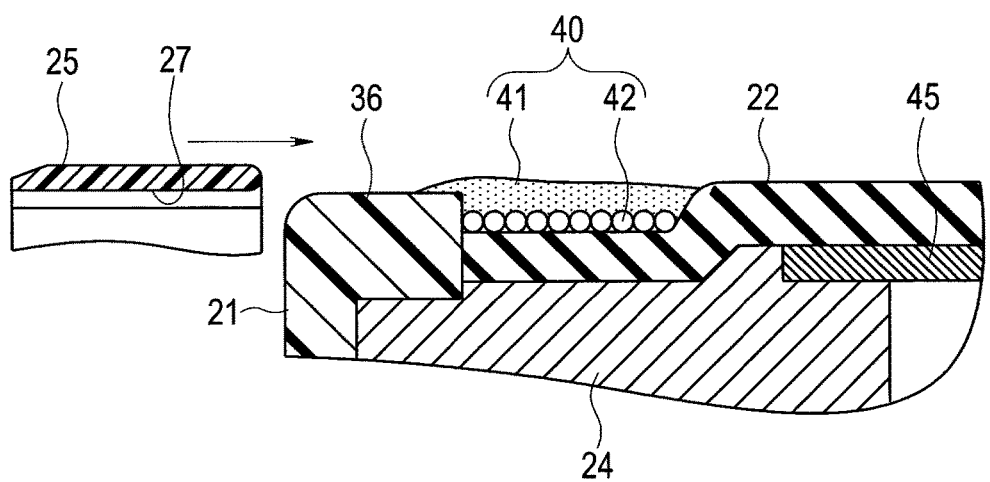
FIG. 7 is a partial cross-sectional view illustrating a state of the first embodiment before the distal-end-side cover member is mounted on a spool adhesion portion.
Figure 8:
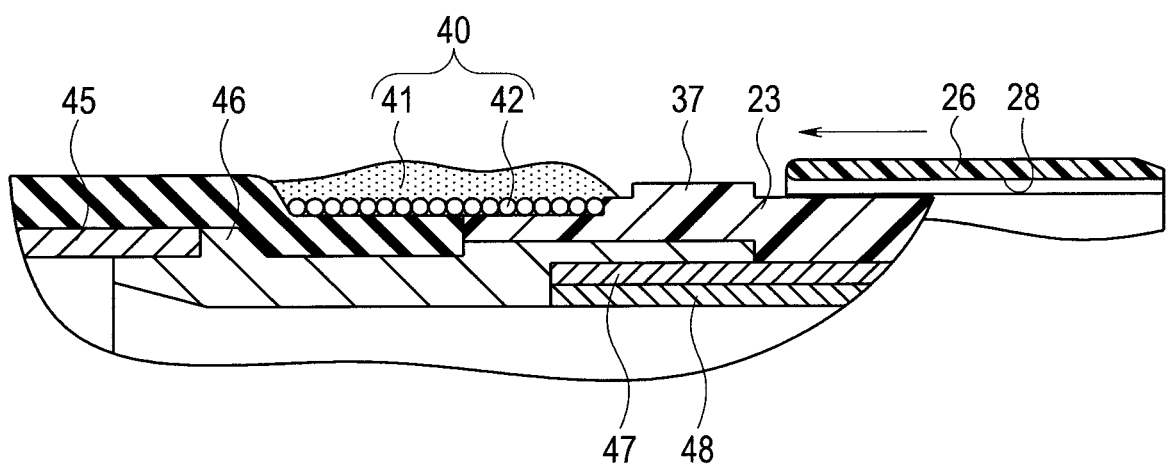
FIG. 8 is a partial cross-sectional view illustrating a state of the first embodiment before the proximal-end-side cover member is mounted on the spool adhesion portion.

A procedure of causing the distal-end-side cover member 25 and the proximal-end-side cover member 26 to be mounted so as to cover the spool adhesion portions 40 is described below. As illustrated in FIG. 6 to FIG. 8, the spool adhesion portions 40 are formed by causing filamentous members 42 to be wound around outer circumferences of both end portions of the bending portion skin 22 such that the filamentous members 42 are fastened tight around the outer circumferences and applying an adhesive agent 41 on outer circumferences of spool portions formed by the winding of the filamentous members 42.

The bending portion skin 22 covers an outer circumferential portion of the distal end frame member 24 (see FIG. 7), has a proximal end portion that covers a connection tube 46 provided in the flexible tube portion 8 fitted with the bending tube 45 (see FIG. 8), and is fixed by the spool adhesion portions 40.

The distal end frame member 24 is a frame body distal end portion of which is fitted with the bending tube 45 in the bending portion 7, and the distal end cap 21 is fixed to the distal end portion by adhesion and the like.

The spool adhesion portion 40 on the proximal end side also fixes the envelope 23 provided so as to cover the connection tube 46 of the flexible tube portion 8. The connection tube 46 is connected to a distal end portion of a spiral tube 48 that is a torque transmission member covered with a braid 47, and the envelope 23 is provided so as to cover an outer circumference of the braid 47. As a result, the flexible tube portion 8 is configured. The envelope 23 may have a structure that is molded by coating.

As illustrated in FIG. 6, the proximal-end-side cover member 26 is arranged to a place around the flexible tube portion 8 of the insertion portion 2 in an inserting manner in advance. At this time, the proximal-end-side cover member 26 is mounted so as to pass through the restricting convex portion 37 in a manner in which circumferential rotation directions are aligned such that the restricting concave portion 28 matches with the restricting convex portion 37 formed on the envelope 23 of the flexible tube portion 8.

After the spool adhesion portions 40 that fix both of the ends of the bending portion skin 22 are formed, the distal-end-side cover member 25 is caused to slide from the distal end side toward the proximal end side as illustrated in FIG. 7, and the proximal-end-side cover member 26 is caused to slide from the proximal end side toward the distal end side as illustrated in FIG. 8. As a result, the distal-end-side cover member 25 and the proximal-end-side cover member 26 are mounted so as to cover the spool adhesion portions 40.

Figure 9:
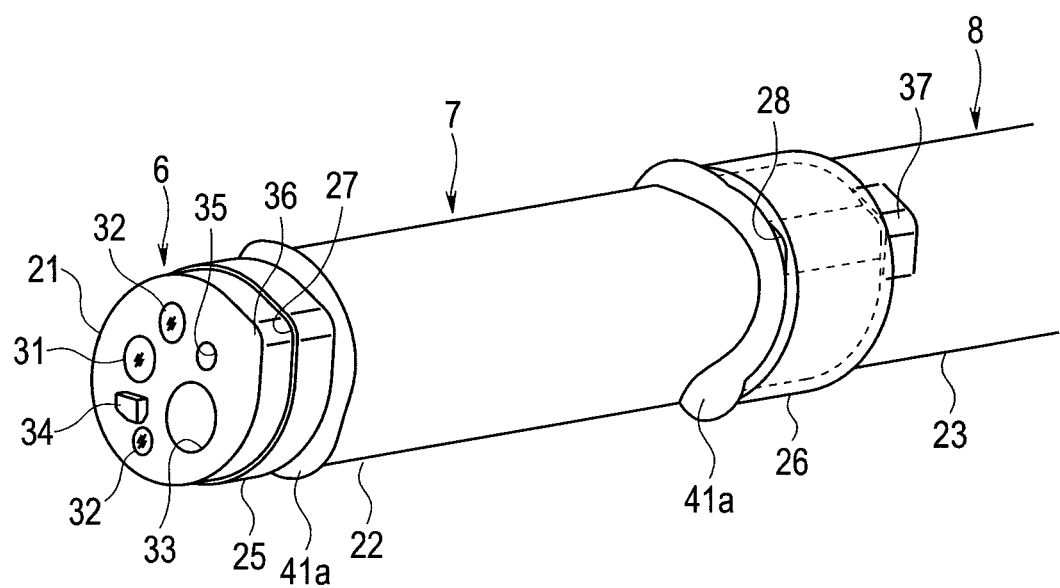
FIG. 9 is a perspective view illustrating a configuration of the distal end portion of the insertion portion of the first embodiment on which the cover member is mounted.
Figure 10:
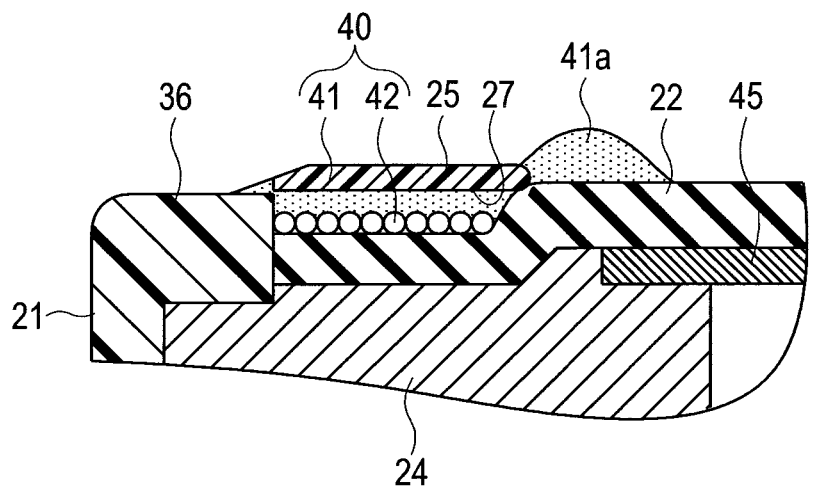
FIG. 10 is a partial cross-sectional view illustrating a state of the first embodiment in which the distal-end-side cover member is mounted on the spool adhesion portion.

More specifically, as illustrated in FIG. 9 and FIG. 10, the distal-end-side cover member 25 is moved toward the proximal end side in a manner in which circumferential rotation directions are aligned such that the restricting concave portion 27 matches with the restricting convex portion 36 of the distal end cap 21, and the distal-end-side cover member 25 is mounted to a position in which the adhesive agent 41 that is a resin portion of the spool adhesion portion 40 on the distal end side is covered.

At this time, in accordance with the movement of the distal-end-side cover member 25, most of an excess adhesive agent 41a is pushed out to the proximal end side of the distal-end-side cover member 25, and is placed in a state of oozing out and being raised from a surface of the bending portion skin 22. The excess adhesive agent 41a also slightly oozes out to the distal end side of the distal-end-side cover member 25.

Figure 11:
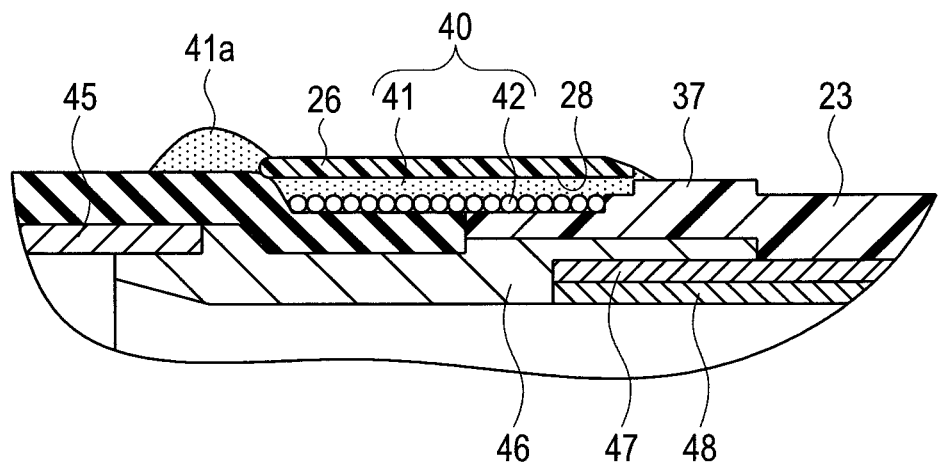
FIG. 11 is a partial cross-sectional view illustrating a state of the first embodiment in which the proximal-end-side cover member is mounted on the spool adhesion portion.

As illustrated in FIG. 9 and FIG. 11, the proximal-end-side cover member 26 is moved toward the distal end side in a manner in which the circumferential rotation directions are aligned such that the restricting concave portion 28 matches with the restricting convex portion 37 of the envelope 23, and the proximal-end-side cover member 26 is mounted to a position in which the adhesive agent of the spool adhesion portion 40 on the proximal end side is covered.

At this time, in accordance with the movement of the proximal-end-side cover member 26, most of the excess adhesive agent 41a is pushed out to the distal end side of the proximal-end-side cover member 26, and is placed in a state of oozing out and being raised from the surface of the bending portion skin 22. The excess adhesive agent 41a also slightly oozes out to the proximal end side of the proximal-end-side cover member 26.

Figure 12:
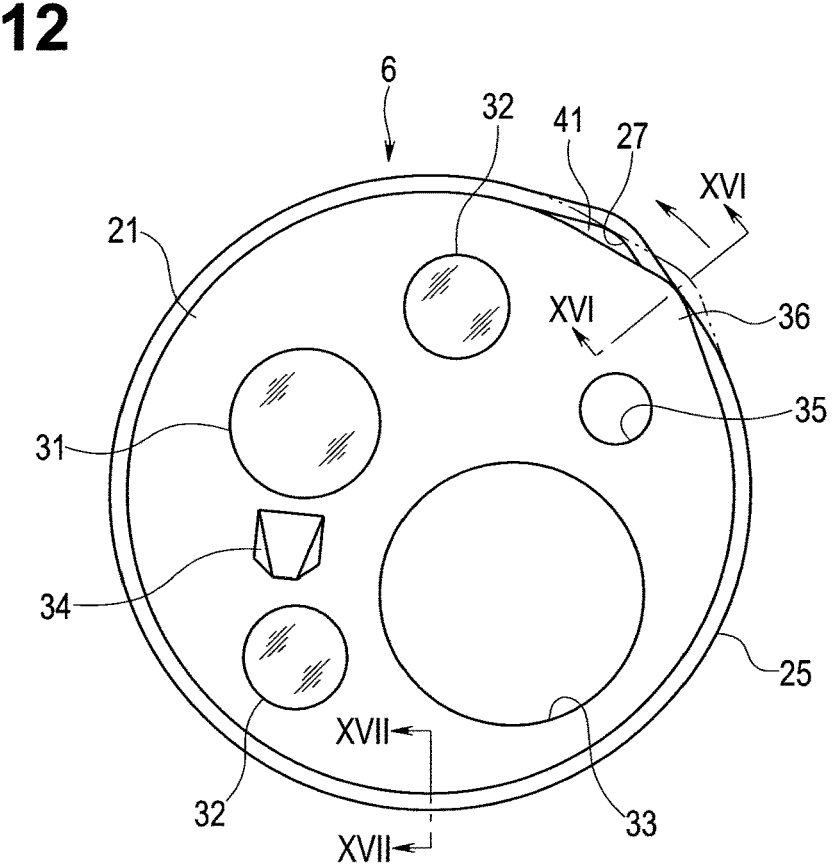
FIG. 12 is a front view of the distal end portion illustrating a state of the first embodiment in which the distal-end-side cover member is rotated.
Figure 13:
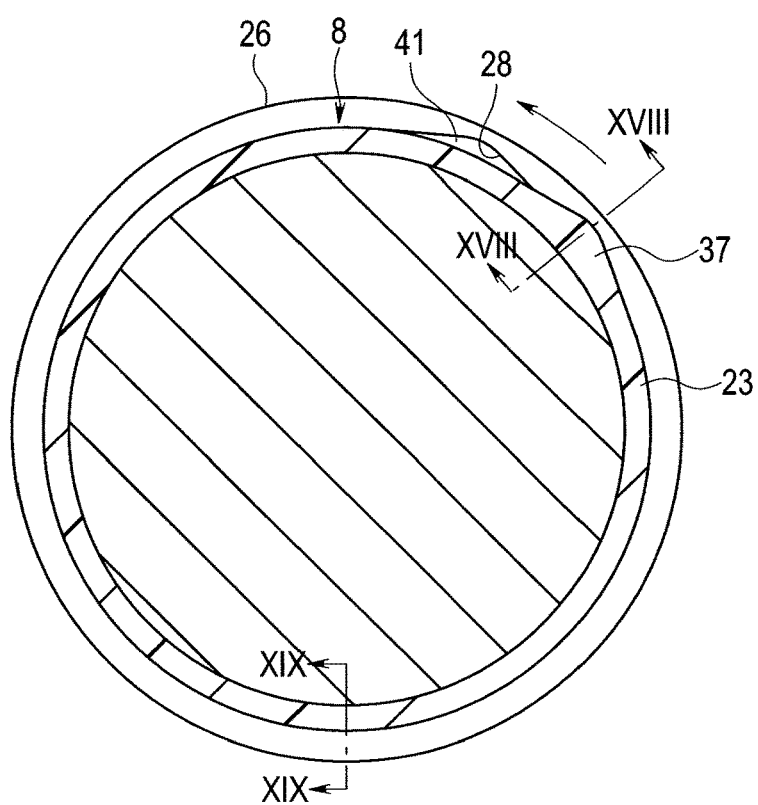
FIG. 13 is a cross-sectional view illustrating a state of the first embodiment in which the proximal-end-side cover member is rotated.

As illustrated in FIG. 12 and FIG. 13, in the distal-end-side cover member 25 and the proximal-end-side cover member 26, the respective restricting concave portions 27 and 28 are rotated about an outer circumference of the bending portion skin 22 of the bending portion 7 at a predetermined angle to positions shifted from the restricting convex portions 36 and 37 in the circumferential direction.

In other words, the restricting concave portion 27 of the distal-end-side cover member 25 is placed in a state of being shifted from the restricting convex portion 36 on the distal end side in the circumferential direction, and the restricting concave portion 28 of the proximal-end-side cover member 26 is placed in a state of being shifted from the restricting convex portion 37 on the proximal end side in the circumferential direction.

As a result, the distal-end-side cover member 25 and the proximal-end-side cover member 26 are mounted in predetermined appropriate positions in which the spool adhesion portions 40 are covered in a state in which one end portion (end surface) facing the restricting convex portion 36 and one end portion (end surface) facing the restricting convex portion 37 abut against the restricting convex portion 36 and the restricting convex portion 37.

Figure 14:
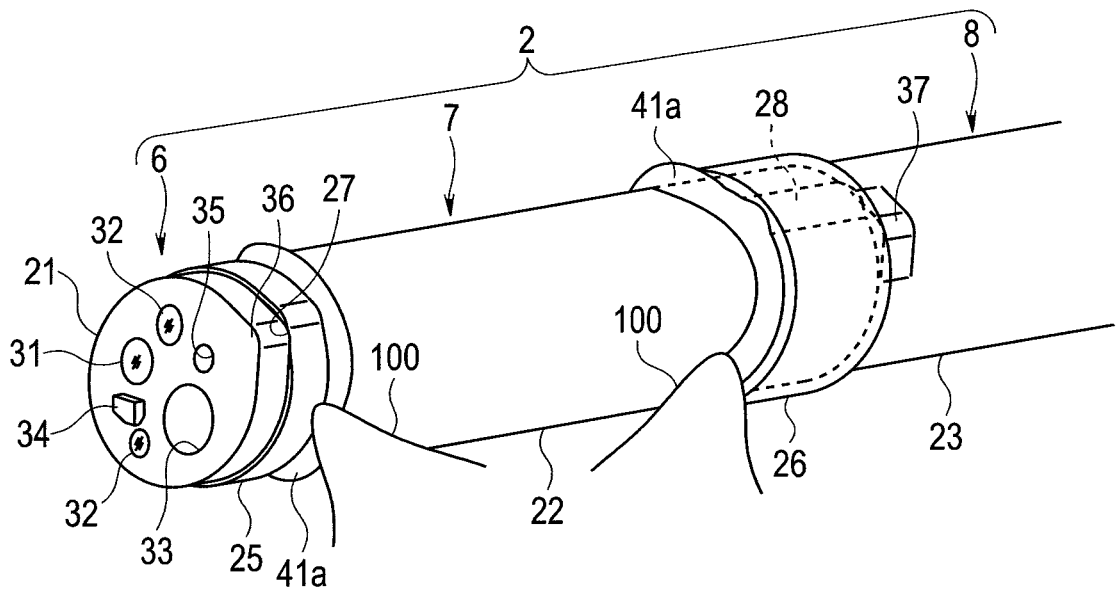
FIG. 14 is a perspective view of the distal end portion of the insertion portion of the first embodiment illustrating a state in which an excess adhesive agent is wiped off.
Figure 15:
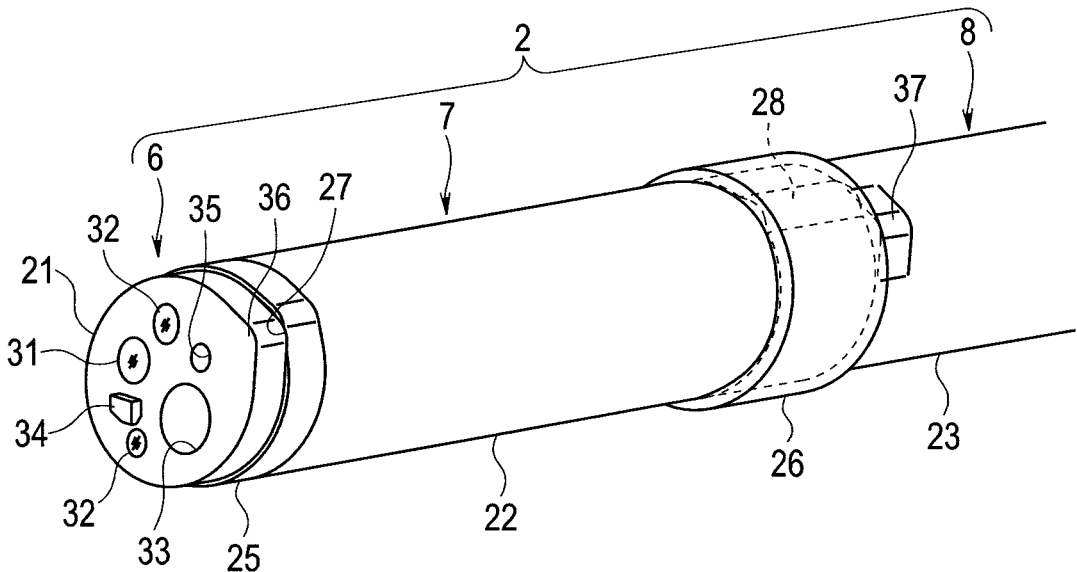
FIG. 15 is a perspective view of the distal end portion of the insertion portion of the first embodiment illustrating a state in which the excess adhesive agent has been wiped off.

By waste cloth 100 and the like as illustrated in FIG. 14, the adhesive agent 41a that has oozed out is wiped off from both ends of the distal-end-side cover member 25 and both ends of the proximal-end-side cover member 26 as illustrated in FIG. 15.

When wipe off is performed as above, the adhesive agent 41a that has oozed out may be wiped off such that gentle slopes or curved shapes are caused to be formed (parts with symbol C illustrated in FIG. 16 to FIG. 19) in order to prevent edges on both end portions of the distal-end-side cover member 25 and both end portions of the proximal-end-side cover member 26 from being left in a formed state.

As illustrated in FIG. 16 to FIG. 19, in the bending portion skin 22 of the bending portion 7, the filamentous members 42 of the spool adhesion portions 40 are wound around outer circumferential portions of both of the ends. As a result, the outer circumferential portions are pressed down in a radially inward direction, outer diameters of the outer circumferential portions become smaller than inner diameters of the distal-end-side cover member 25 and the proximal-end-side cover member 26, and outer diameters of parts other than the outer circumferential portions become large.

Figure 16:
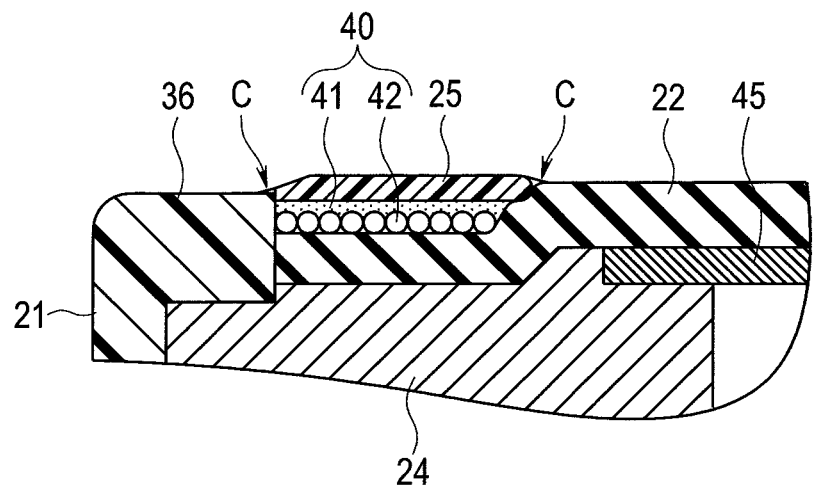
FIG. 16 is a partial cross-sectional view of the distal end portion of the first embodiment taken along line XVI-XVI in FIG. 12.
Figure 17:
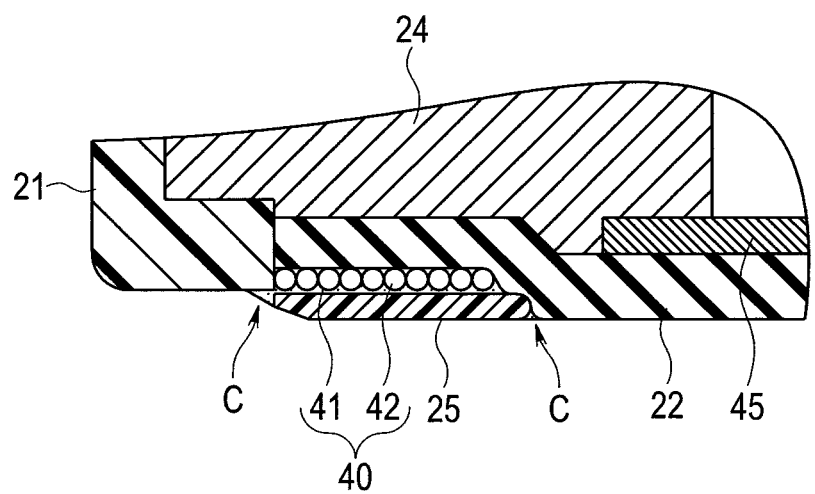
FIG. 17 is a partial cross-sectional view of the distal end portion of the first embodiment taken along line XVII-XVII in FIG. 12.
Figure 18:
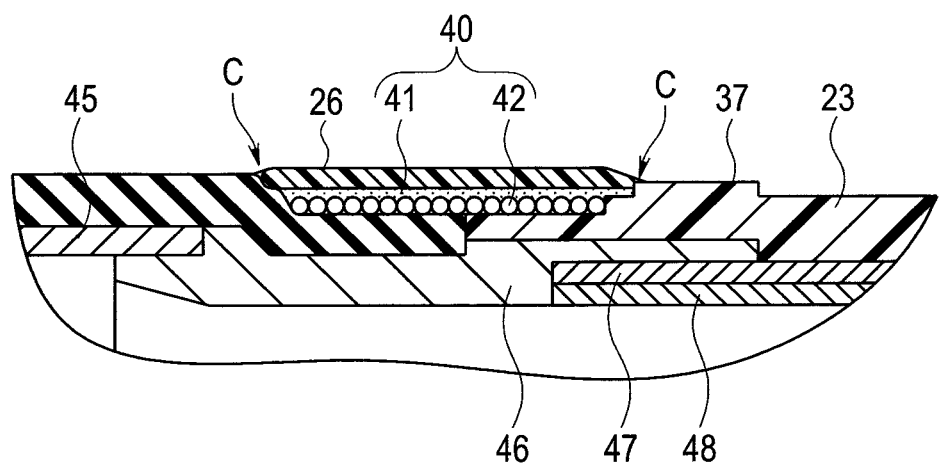
FIG. 18 is a partial cross-sectional view of a proximal end side of a bending portion of the first embodiment taken along line XVIII-XVIII in FIG. 13.
Figure 19:
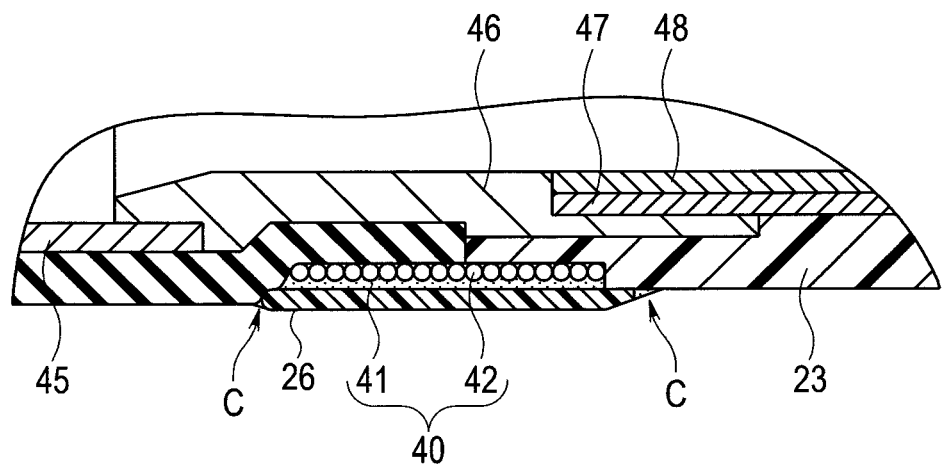
FIG. 19 is a partial cross-sectional view of the proximal end side of the bending portion of the first embodiment taken along line XIX-XIX in FIG. 13.

As a result, the distal-end-side cover member 25 and the proximal-end-side cover member 26 are placed in a state of being sandwiched between the bending portion skin 22 and the restricting convex portions 36 and 37, and are held in a state of hardly rotating even in wipe off operation of the adhesive agent 41a that has oozed out in addition to being prevented from moving in the front-rear direction (see FIG. 16 and FIG. 18).

Heat hardening treatment of the adhesive agent 41 of the spool adhesion portions 40 is performed at about 60° C. and the distal-end-side cover member 25 and the proximal-end-side cover member 26 are fixed to the spool adhesion portions 40.

As described above, in the endoscope 1 of the embodiment, the annular distal-end-side cover member 25 and the annular proximal-end-side cover member 26 can be placed in predetermined appropriate positions in which the spool adhesion portions 40 that fix both of the end portions of the bending portion skin 22 of the bending portion 7 are covered, and the excess adhesive agent 41a that has oozed out can be easily wiped off from both of the end portions of the distal-end-side cover member 25 and both of the end portions of the proximal-end-side cover member 26 held by being in abutment against the restricting convex portions 36 and 37.

In other words, in the endoscope 1, before the heat hardening treatment of the spool adhesion portions 40 provided on both end portions of the bending portion 7 of the insertion portion 2, the distal-end-side cover member 25 and the proximal-end-side cover member 26 that cover the spool adhesion portions 40 are placed in a state of being held so as not to move from predetermined appropriate positions, and hence the excess adhesive agent 41a can be easily wiped clean and the time period for the wipe off operation of the adhesive agent 41a can also be significantly shortened as compared to the related art.

From the above, the endoscope 1 of the embodiment has a configuration in which the distal-end-side cover member 25 and the proximal-end-side cover member 26 that prevent deterioration due to medicinal solution and the like at the time of cleaning and sterilization of the spool adhesion portions 40 that fix both of the end portions of the bending portion skin 22 serving as a bending-portion envelope are provided, and the excess adhesive agent 41a of the spool adhesion portions 40 at the time of assembly of the distal-end-side cover member 25 and the proximal-end-side cover member 26 is wiped clean in a short time period, and the working property is improved.

The restricting convex portions 36 and 37 may also be provided on the bending portion skin 22 side, and the distal-end-side cover member 25 may be held by two restricting convex portions 36 and the proximal-end-side cover member 26 may be held by two restricting convex portions 37, so as to be sandwiched in the front-rear direction.

(First Modification)

Figure 20:
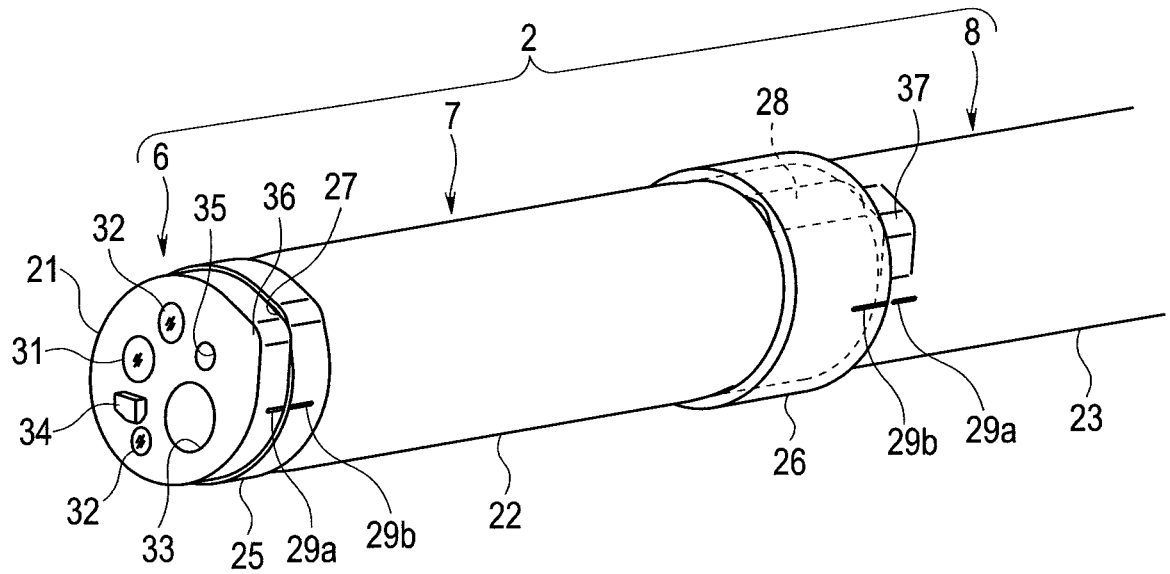
FIG. 20 is a perspective view illustrating a configuration of the distal end portion of the insertion portion of a first modification of the first embodiment.

As illustrated in FIG. 20, indices 29a and 29b in a line form and the like that define rotation positions of the distal-end-side cover member 25 and the proximal-end-side cover member 26 may be provided such that the restricting concave portions 27 and 28 of the distal-end-side cover member 25 and the proximal-end-side cover member 26 are placed in positions shifted from the restricting convex portions 36 and 37 in the circumferential direction.

The indices 29a and 29b are provided on outer circumferential surfaces of the distal-end-side cover member 25 and the proximal-end-side cover member 26, an outer circumferential surface of the distal end cap 21 of the distal end portion 6, and an outer circumferential surface of the envelope 23 of the flexible tube portion 8 by printing, molding, and the like.

(Second Modification)

Figure 21:
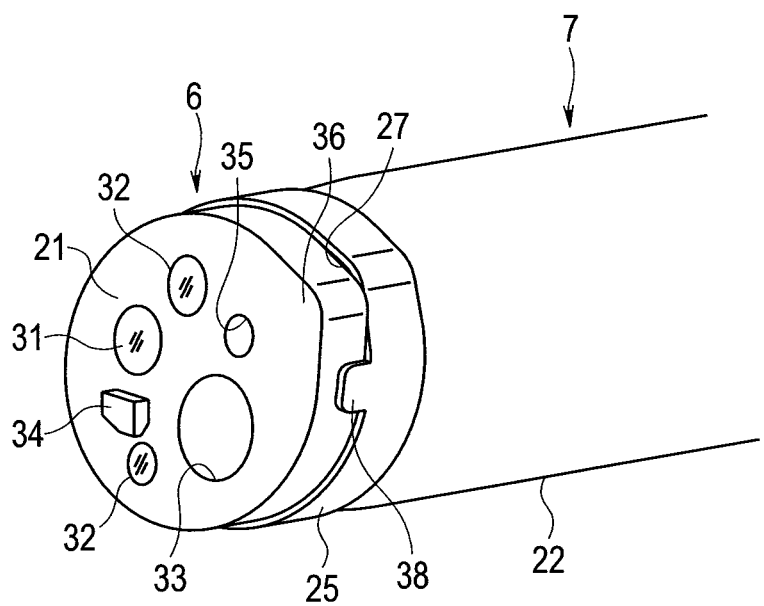
FIG. 21 is a perspective view illustrating a configuration of a distal end portion of an insertion portion of a second modification of the first embodiment.

As illustrated in FIG. 21, in the distal-end-side cover member 25, a stopper 38 that is a protrusion piece that protrudes from an end portion facing the restricting convex portion 36 may be provided, and the rotation position of the distal-end-side cover member 25 may be defined such that the restricting concave portion 27 is placed in a position shifted from the restricting convex portion 36 in the circumferential direction.

When the distal-end-side cover member 25 rotates, the stopper 38 comes into contact with the restricting convex portion 36 and the distal-end-side cover member 25 is prevented from rotating any further. As a result, the rotation position is defined. Needless to say, the stopper 38 that defines the rotation position may also be provided on the proximal-end-side cover member 26.

(Third Modification)

Figure 22:
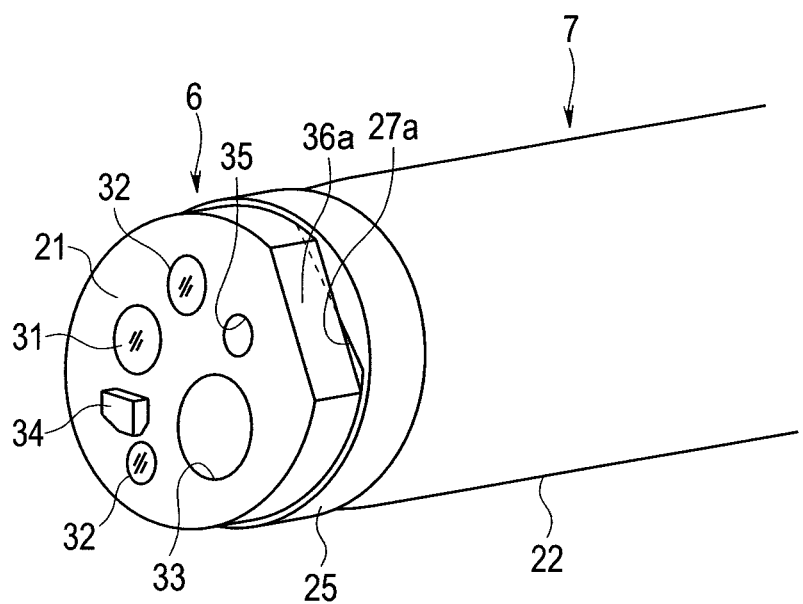
FIG. 22 is a perspective view illustrating a configuration of a distal end portion of an insertion portion of a third modification of the first embodiment.

As illustrated in FIG. 22, a plane surface 36a may be formed by cutting the distal end cap 21 into a D-cut shape, a plane surface 27a may be formed such that an inner surface of the distal-end-side cover member 25 has a shape homothetic to an outer surface shape of the distal end cap 21, and the distal-end-side cover member 25 may be held by abutting against the distal end cap 21.

It has been described that the outer surface shape of the distal end cap 21 and an inner surface shape of the distal-end-side cover member 25 have homothetic shapes by the respective plane surfaces 36a and 27a, but the term "homothetic" is not limited to having substantially similar shapes, and the distal-end-side cover member 25 only needs to have a shape that is held by abutting against the distal end cap 21.

With respect to the embodiment above, an embodiment in which the relationship between the protrusion provided on the outer surface of the insertion portion 2 of the endoscope 1 and the concave portion provided in the cover member is reversed can be conceived.

In other words, the insertion portion 2 of the endoscope 1 may have, in one part of the outer surface in the circumferential direction, a concave portion that is narrower than other parts in a radial direction, and the cover member (the distal-end-side cover member 25 or the proximal-end-side cover member 26) mounted so as to cover the adhesive agent 41 that is a resin portion of the spool adhesion portion 40 may have a protruding portion provided in a manner of protruding from the inner circumferential surface so as to be disposed in a position shifted from the concave portion in the circumferential direction of the insertion portion and have a cross-sectional shape substantially homothetic to a cross-sectional shape of the concave portion.

As a specific example of the above, as illustrated in FIG. 22, a configuration in which the plane surface 36a is formed by cutting the distal end cap 21 in a D-cut shape, the plane surface 27a is formed such that the inner surface of the distal-end-side cover member 25 has a shape homothetic to the outer surface shape of the distal end cap 21, and the distal-end-side cover member 25 held by abutting against the distal end cap 21 can be conceived. The effects obtained by the embodiment are almost the same as the effects of the first embodiment.

Second Embodiment

The endoscope 1 of the second embodiment of the embodiments is described in detail below.

Figure 23:
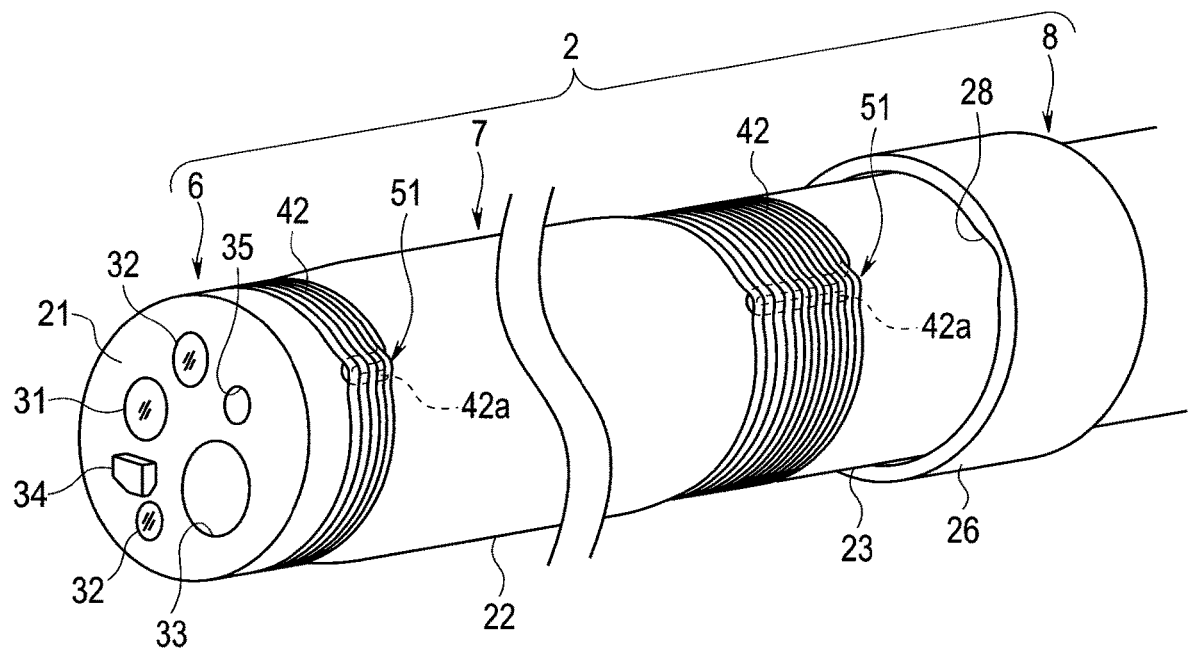
FIG. 23 is a perspective view illustrating a configuration of a distal end portion of an insertion portion of a second embodiment.

As illustrated in FIG. 23, in the endoscope 1 of the embodiment, instead of the restricting convex portions 36 and 37 of the first embodiment, end portions 42a at which the winding of the filamentous members 42 of the spool adhesion portions 40 for fixing both of the end portions of the bending portion skin 22 of the bending portion 7 around the bending portion skin 22 is started are bent on the surface of the bending portion skin 22, the filamentous members 42 are wound around a place on the bent end portions 42a, and restricting convex portions 51 that are partially raised are formed. In other words, the restricting convex portions 51 are formed by stacking the filamentous members 42 in a radial direction of the insertion portion 2.

Figure 24:
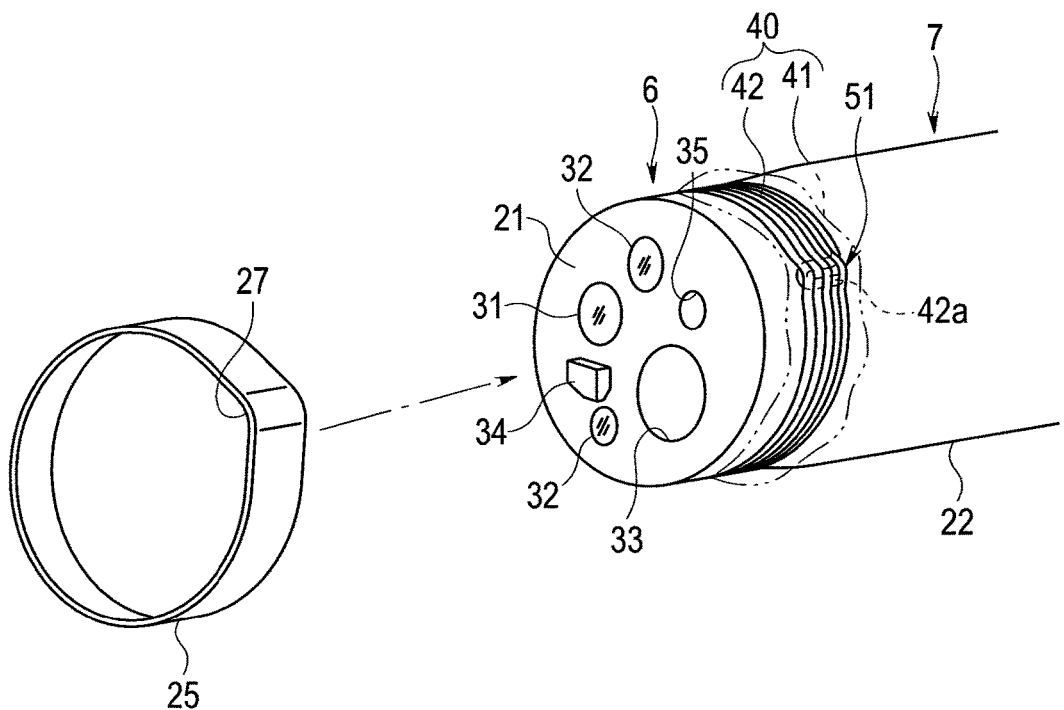
FIG. 24 is a perspective view illustrating a configuration of the distal end portion of the insertion portion of the second embodiment on which a distal-end-side cover member is to be mounted.

The proximal-end-side cover member 26 is also arranged to a place around the flexible tube portion 8 of the insertion portion 2 in an inserting manner in advance here. After the spool adhesion portions 40 that fix both of the ends of the bending portion skin 22 are formed, the distal-end-side cover member 25 is caused to slide from the distal end side toward the proximal end side and is mounted so as to cover the spool adhesion portion 40 on the distal end side as illustrated in FIG. 24.

As with the distal-end-side cover member 25, the proximal-end-side cover member 26 is also caused to slide from the proximal end side toward the distal end side and is mounted so as to cover the spool adhesion portion 40 on the proximal end side.

The distal-end-side cover member 25 is moved toward the proximal end side in a manner in which the circumferential rotation directions are aligned such that the restricting concave portion 27 matches with the restricting convex portion 51 of the spool adhesion portion 40 on the distal end side, and the distal-end-side cover member 25 is mounted to a position in which the adhesive agent 41 that is a resin portion of the spool adhesion portion 40 on the distal end side is covered.

The proximal-end-side cover member 26 is moved toward the distal end side in a manner in which the circumferential rotation directions are aligned such that the restricting concave portion 28 matches with the restricting convex portion 51 of the spool adhesion portion 40 on the proximal end side, and the proximal-end-side cover member 26 is mounted to a position in which the adhesive agent of the spool adhesion portion 40 on the proximal end side is covered.

Figure 25:
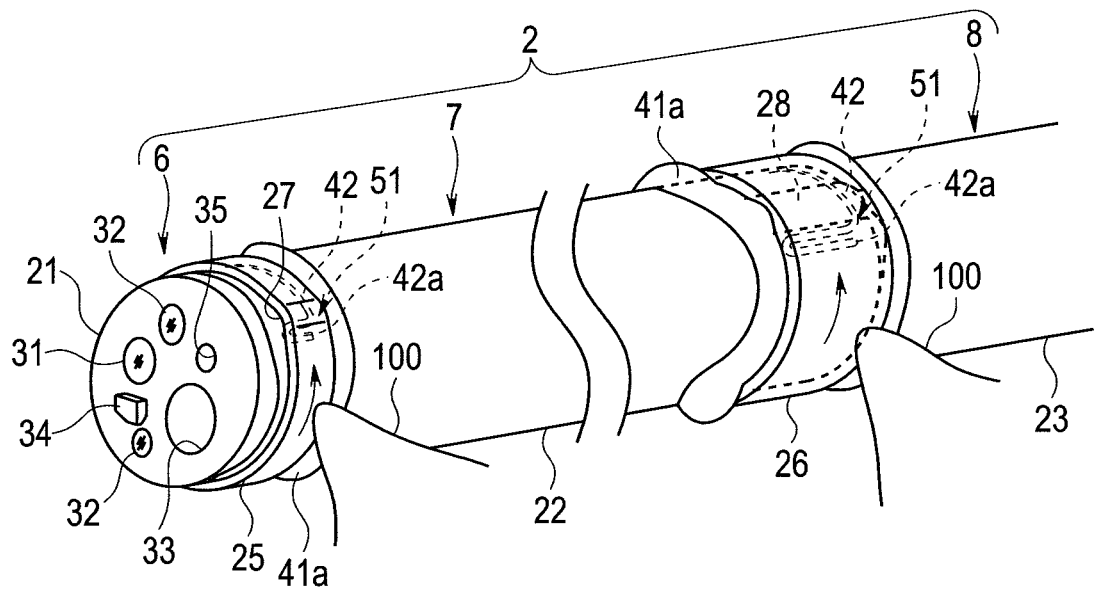
FIG. 25 is a perspective view of the distal end portion of the insertion portion of the second embodiment illustrating a state in which an excess adhesive agent is wiped off.
Figure 26:
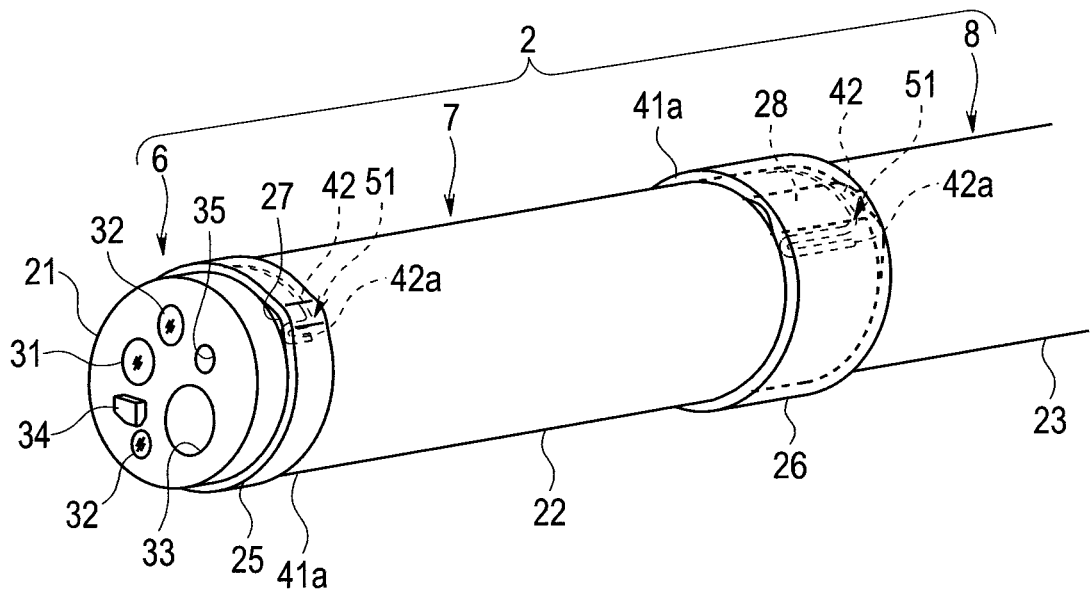
FIG. 26 is a perspective view of the distal end portion of the insertion portion of the second embodiment illustrating a state in which the excess adhesive agent has been wiped off.

As illustrated in FIG. 25, in the distal-end-side cover member 25 and the proximal-end-side cover member 26, the respective restricting concave portions 27 and 28 are caused to rotate about the outer circumference of the bending portion skin 22 of the bending portion 7 at a predetermined angle to a position shifted from the restricting convex portions 51 in the circumferential direction.

As a result, the restricting concave portion 27 of the distal-end-side cover member 25 is placed in a state of being shifted from the restricting convex portion 51 on the distal end side in the circumferential direction, and the restricting concave portion 28 of the proximal-end-side cover member 26 is placed in a state of being shifted from the restricting convex portion 51 on the proximal end side in the circumferential direction.

At this time, the distal-end-side cover member 25 and the proximal-end-side cover member 26 are mounted in predetermined appropriate positions in which the spool adhesion portions 40 are covered in a state in which the restricting convex portions 51 abut against the inner circumferential surfaces.

By waste cloth 100 and the like, the adhesive agent 41a that has oozed out is wiped off from both of the ends of the distal-end-side cover member 25 and both of the ends of the proximal-end-side cover member 26.

At the time of the wipe off operation of the adhesive agent 41a that has oozed out, inner surfaces of the distal-end-side cover member 25 and the proximal-end-side cover member 26 abut against the restricting convex portions 51 raised from both ends of the bending portion skin 22 and are pressed against both of the ends in the radially inward direction, and hence the distal-end-side cover member 25 and the proximal-end-side cover member 26 are placed in a state of being held without rotating and not moving in the front-rear direction.

Then, the heat hardening treatment of the adhesive agent 41 of the spool adhesion portions 40 is performed, and the distal-end-side cover member 25 and the proximal-end-side cover member 26 are fixed to the spool adhesion portions 40.

Even with the configuration as above, as with the above-mentioned first embodiment, the endoscope 1 of the embodiment has a configuration in which the distal-end-side cover member 25 and the proximal-end-side cover member 26 that prevent deterioration due to medicinal solution and the like at the time of the cleaning and sterilization of the spool adhesion portions 40 that fix both of the end portions of the bending portion skin 22 serving as the bending-portion envelope are provided, the excess adhesive agent 41a of the spool adhesion portions 40 at the time of assembly of the distal-end-side cover member 25 and the proximal-end-side cover member 26 is wiped clean in a short time period, and the working property is improved.

(Modification)

Figure 27:
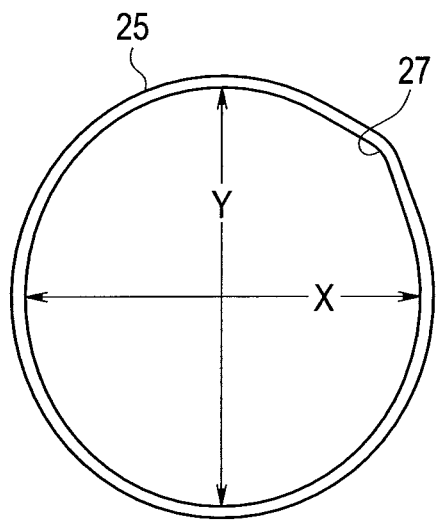
FIG. 27 is a plan view illustrating a configuration of a distal-end-side cover member of a modification of the second embodiment.
Figure 28:
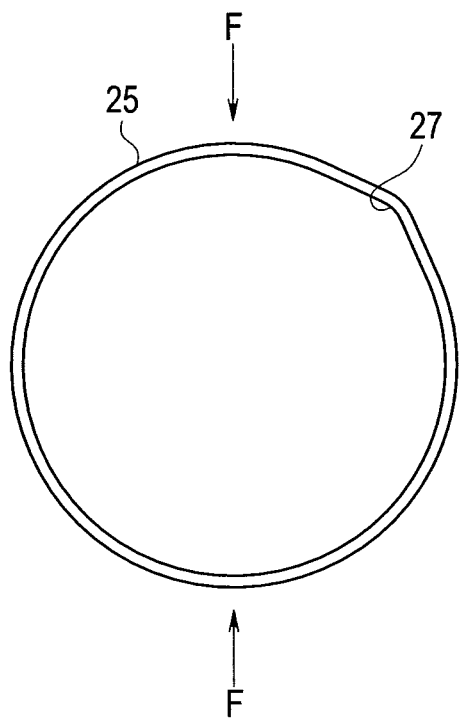
FIG. 28 is a plan view illustrating a configuration of the distal-end-side cover member of the modification of the second embodiment that is deformed by being pressed down along a major axis.

The distal-end-side cover member 25 may be an elliptical annular member that has a predetermined length X in a minor axis and a predetermined length Y (X<Y) in a major axis on an inner surface as illustrated in FIG. 27, and may be mounted on the spool adhesion portion 40 by being deformed by being pressed down with a predetermined force F in the radially inward direction along the major axis with the length Y as illustrated in FIG. 28.

Figure 29:
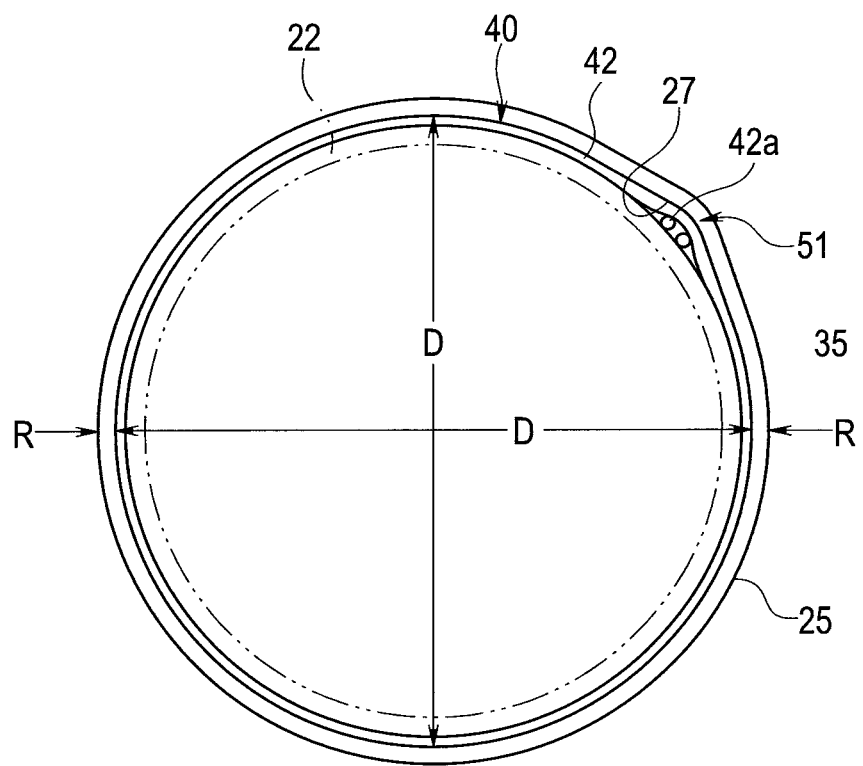
FIG. 29 is a view illustrating a state of the modification of the second embodiment in which a distal-end-side cover member is mounted on a spool adhesion portion.

As illustrated in FIG. 29, the spool portion in which the filamentous member 42 of the spool adhesion portion 40 is wound has a predetermined outer diameter D, and the predetermined outer diameter D is longer than the predetermined length X (D >X) and shorter than the predetermined length Y (D<Y).

Therefore, a predetermined restorative force R is generated in the minor axis direction, and the inner surface presses the spool portion. As a result, the distal-end-side cover member 25 mounted on the spool adhesion portion 40 is placed in a state of being held without rotating and not moving in the front-rear direction even when the restricting concave portion 27 is not in a state of being shifted from the restricting convex portion 51 in the circumferential direction.

Only the distal-end-side cover member 25 is exemplified here, but the proximal-end-side cover member 26 may have a similar configuration.

Third Embodiment

The endoscope 1 of a third embodiment of the embodiments is described in detail below.

The endoscope 1 here has a configuration described in the second embodiment in which the end portions 42a at which the winding of the filamentous members 42 of the spool adhesion portions 40 for fixing both of the end portions of the bending portion skin 22 of the bending portion 7 around the bending portion skin 22 is started are bent on the surface of the bending portion skin 22, the filamentous members 42 are wound around a place on the bent end portions 42a, and the restricting convex portions 51 that are partially raised are formed.

Figure 30:
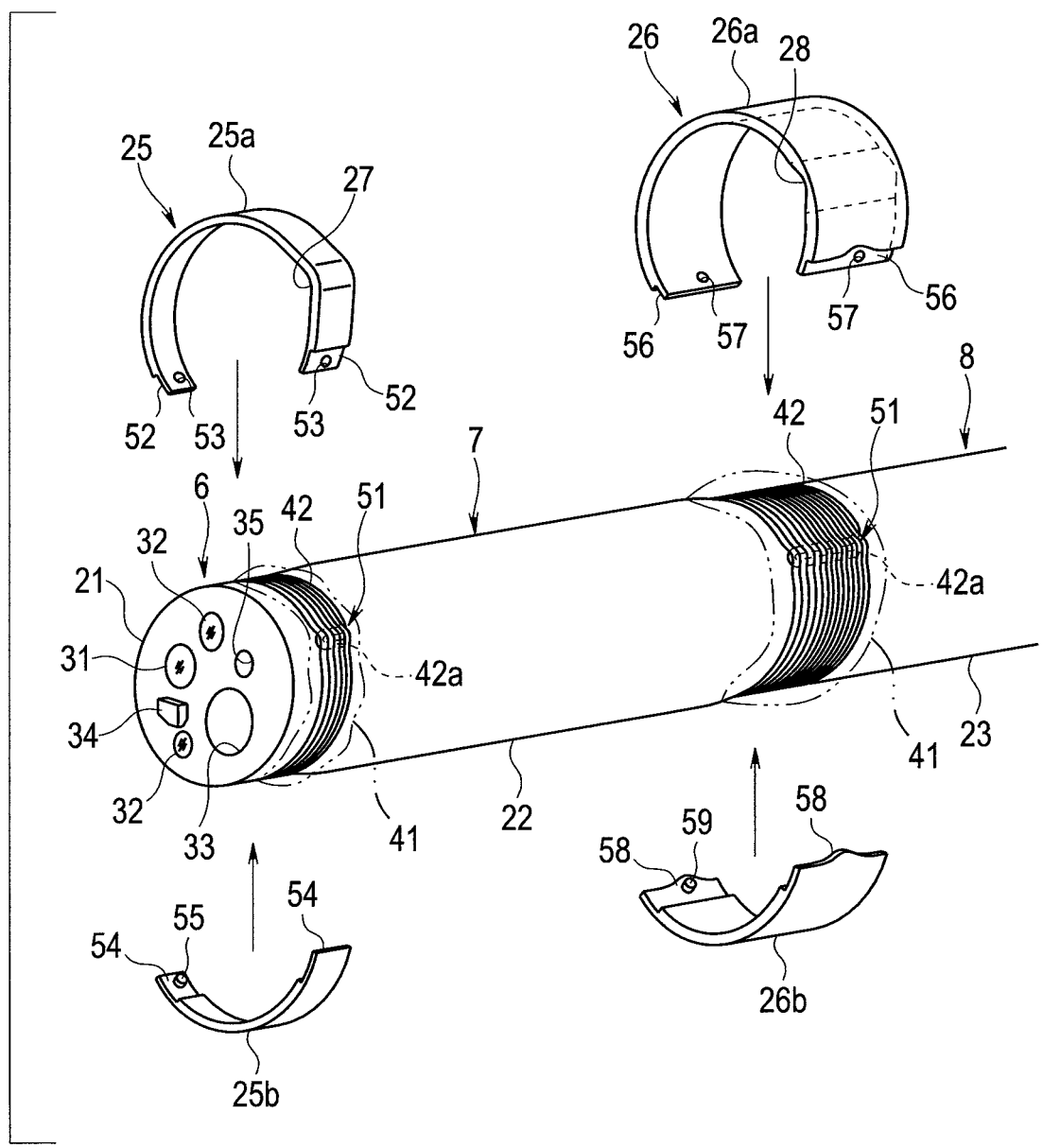
FIG. 30 is an exploded perspective view illustrating a configuration of a distal end portion of an insertion portion of a third embodiment.
Figure 31:
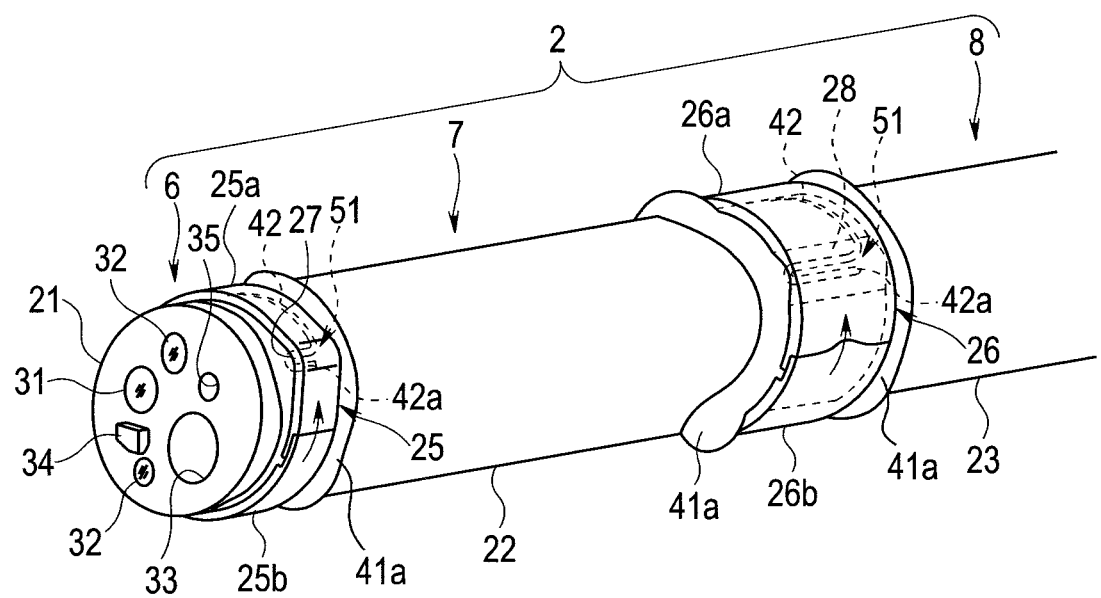
FIG. 31 is a perspective view illustrating a configuration of the distal end portion of the insertion portion of the third embodiment on which a cover member is mounted.

As illustrated in FIG. 30 and FIG. 31, in the endoscope 1, each of the distal-end-side cover member 25 and the proximal-end-side cover member 26 has a two-body structure.

More specifically, the distal-end-side cover member 25 is formed in an annular shape by coupling a first-distal-end-side cover member 25a having an arc shape in cross section and a second distal-end-side cover member 25b having an arc shape in cross section to each other.

In the first-distal-end-side cover member 25a, the restricting concave portion 27 is provided, female-side step portions 52 obtained by cutting out outer sides are formed on both end portions, and a locking hole portion 53 is formed in each of the female-side step portions 52. In the second distal-end-side cover member 25b, male-side step portions 54 are formed by cutting out inner sides of both end portions, and locking pins 55 that protrude from inner surfaces of the male-side step portions 54 are provided.

The female-side step portion 52 and the male-side step portion 54 engage with each other, and the locking pins 55 are inserted into the locking hole portions 53 in an engaged manner. As a result, the first-distal-end-side cover member 25a and the second distal-end-side cover member 25b are coupled to each other, and the annular distal-end-side cover member 25 is formed.

The first-distal-end-side cover member 25a of the distal-end-side cover member 25 is fitted onto an outer circumference of the bending portion 7 in one direction of the outer circumference of the bending portion 7 in a position in which the adhesive agent 41 that is a resin portion of the spool adhesion portion 40 on the distal end side is covered such that the restricting concave portion 27 matches with the restricting convex portion 51 of the spool adhesion portion 40 on the distal end side.

The second distal-end-side cover member 25b of the distal-end-side cover member 25 is mounted by being coupled to the first-distal-end-side cover member 25a in another direction of the outer circumference of the bending portion 7. By the above, the distal-end-side cover member 25 is mounted so as to cover the spool adhesion portion 40 on the distal end side.

The proximal-end-side cover member 26 is formed in an annular shape by coupling a first proximal-end-side cover member 26a having an arc shape in cross section and a second proximal-end-side cover member 26b having an arc shape in cross section to each other.

In the first proximal-end-side cover member 26a, the restricting concave portion 28 is provided, female-side step portions 56 obtained by cutting out outer sides are formed on both end portions, and a locking hole portion 57 is formed in each of the female-side step portions 56. In the second proximal-end-side cover member 26b, male-side step portions 58 are formed by cutting out inner sides of both end portions, and locking pins 59 that protrude from inner surfaces of the male-side step portions 58 are provided.

The female-side step portion 56 and the male-side step portion 58 engage with each other, and the locking pins 59 are inserted into the locking hole portions 57 in an engaged manner. As a result, the first proximal-end-side cover member 26a and the second proximal-end-side cover member 26b are coupled to each other, and the annular proximal-end-side cover member 26 is formed.

The first proximal-end-side cover member 26a of the proximal-end-side cover member 26 is fitted onto the outer circumference of the bending portion 7 in one direction of the outer circumference of the bending portion 7 in a position in which the adhesive agent 41 that is a resin portion of the spool adhesion portion 40 on the distal end side is covered such that the restricting concave portion 28 matches with the restricting convex portion 51 of the spool adhesion portion 40 on the proximal end side.

The second proximal-end-side cover member 26b of the proximal-end-side cover member 26 is mounted in an outer direction of the bending portion 7 by being coupled to the first proximal-end-side cover member 26a. By the above, the proximal-end-side cover member 26 is mounted so as to cover the spool adhesion portion 40 on the proximal end side.

In the distal-end-side cover member 25 and the proximal-end-side cover member 26 mounted so as to cover the spool adhesion portions 40 as above, the respective restricting concave portions 27 and 28 are caused to rotate about the outer circumference of the bending portion skin 22 of the bending portion 7 at a predetermined angle to a position shifted from the restricting convex portions 51 in the circumferential direction.

Figure 32:
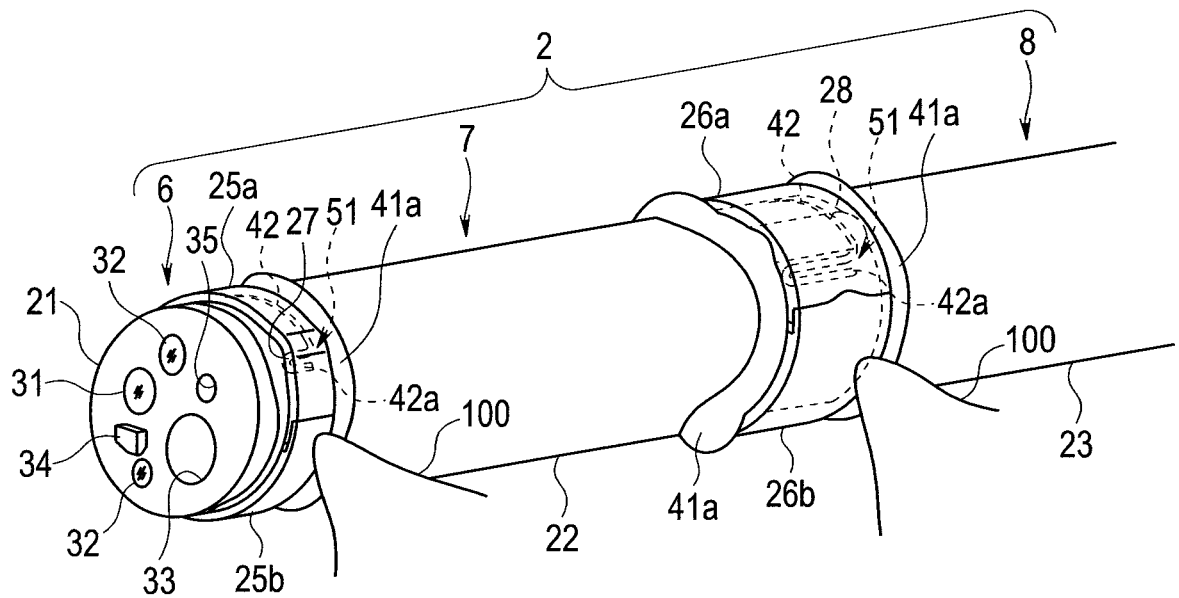
FIG. 32 is a perspective view of the distal end portion of the insertion portion of the third embodiment illustrating a state in which an excess adhesive agent is wiped off.

As illustrated in FIG. 32, by the waste cloth 100 and the like, the adhesive agent 41a that has oozed out is wiped off from both ends of the distal-end-side cover member 25 and the proximal-end-side cover member 26.

At the time of the wipe off operation of the adhesive agent 41a that has oozed out, inner surfaces of the distal-end-side cover member 25 and the proximal-end-side cover member 26 abut against the restricting convex portions 51 raised from both ends of the bending portion skin 22 and are pressed against both of the ends in the radially inward direction, and hence the distal-end-side cover member 25 and the proximal-end-side cover member 26 are placed in a state of being held without rotating and not moving in the front-rear direction.

Figure 33:
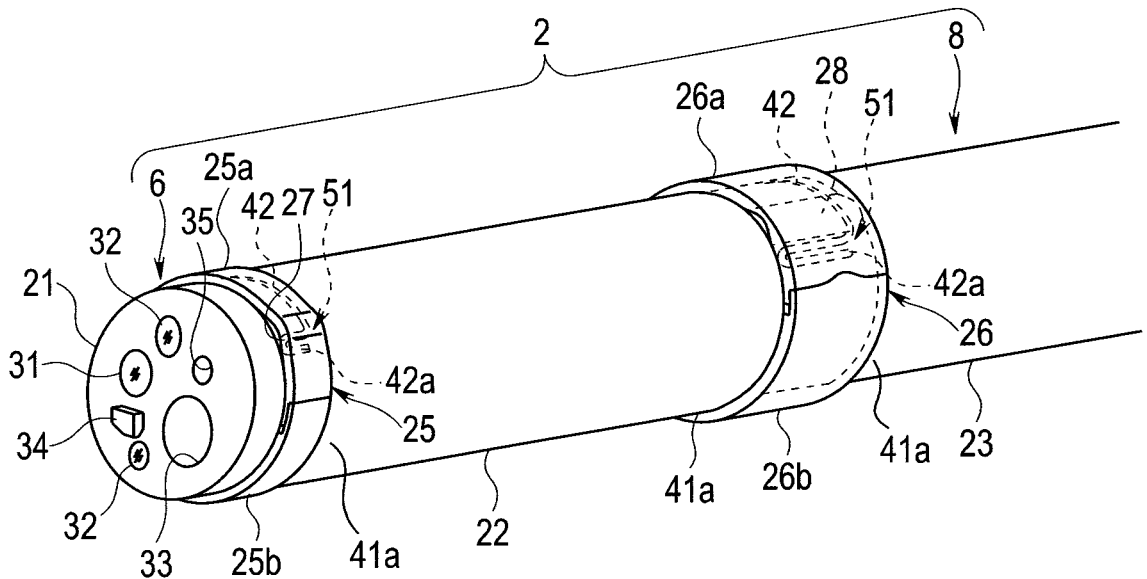
FIG. 33 is a perspective view of the distal end portion of the insertion portion of the third embodiment illustrating a state in which the excess adhesive agent has been wiped off.

Then, the heat hardening treatment of the adhesive agent 41 of the spool adhesion portions 40 is performed, and the distal-end-side cover member 25 and the proximal-end-side cover member 26 are fixed to the spool adhesion portions 40 as illustrated in FIG. 33.

Even with the configuration as above, as with the first and second embodiments described above, the endoscope 1 of the embodiment has a configuration in which the distal-end-side cover member 25 and the proximal-end-side cover member 26 that prevent deterioration due to medicinal solution and the like at the time of the cleaning and sterilization of the spool adhesion portions 40 that fix both of the end portions of the bending portion skin 22 serving as the bending-portion envelope are provided, the excess adhesive agent 41a of the spool adhesion portions 40 at the time of assembly of the distal-end-side cover member 25 and the proximal-end-side cover member 26 is wiped clean in a short time period, and the working property is improved.

(First Modification)

Figure 34:
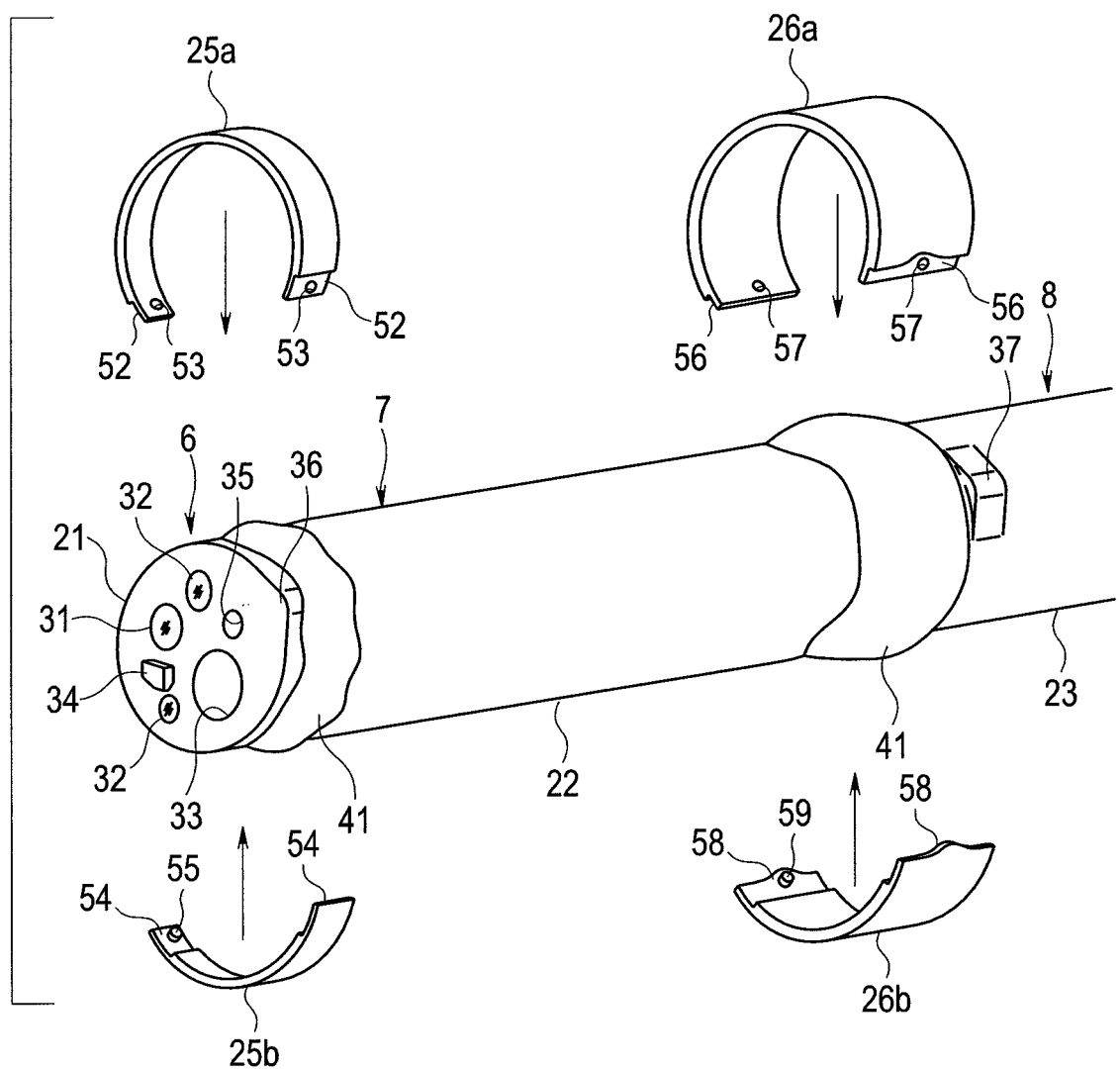
FIG. 34 is an exploded perspective view illustrating a configuration of a distal end portion of an insertion portion of a first modification of the third embodiment.
Figure 35:
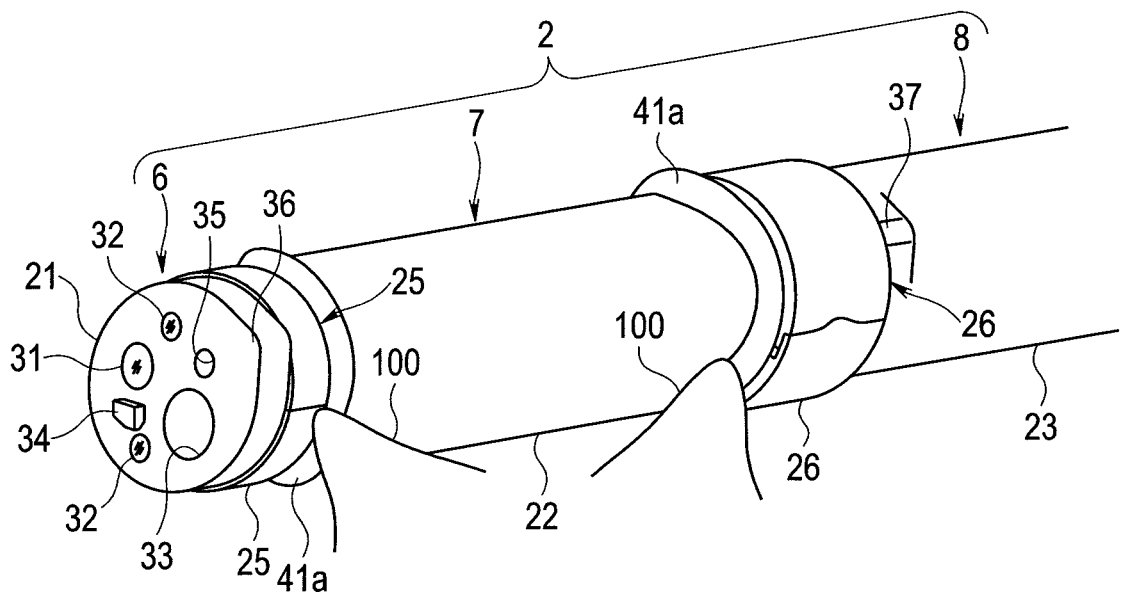
FIG. 35 is a perspective view of the distal end portion of the insertion portion of the first modification of the third embodiment illustrating a state in which an excess adhesive agent is wiped off.
Figure 36:
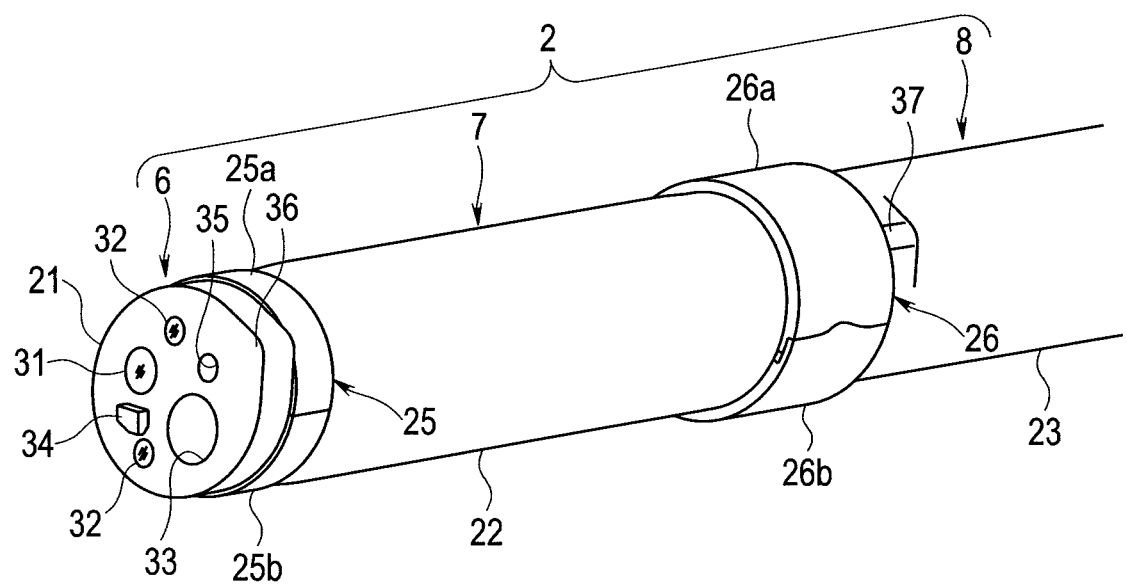
FIG. 36 is a perspective view of the distal end portion of the insertion portion of the first modification of the third embodiment illustrating a state in which the excess adhesive agent has been wiped off.

As illustrated in FIG. 34 to FIG. 36, each of the distal-end-side cover member 25 and the proximal-end-side cover member 26 may have a two-body structure in the endoscope 1 in which the restricting convex portions 36 and 37 described in the first embodiment are provided as well. The restricting concave portions 27 and 28 do not necessarily need to be provided in the first-distal-end-side cover member 25a and the first proximal-end-side cover member 26a.

(Second Modification)

Figure 37:
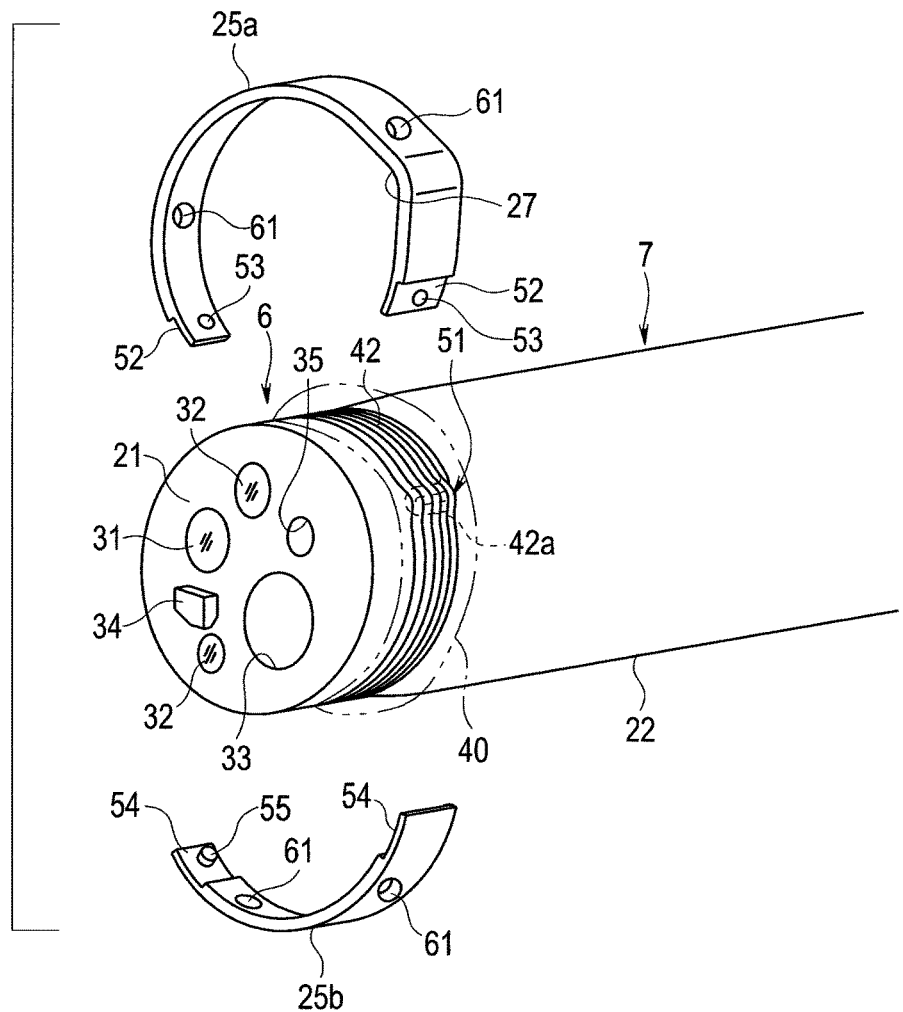
FIG. 37 is an exploded perspective view illustrating a configuration of a distal end portion of an insertion portion of a second modification of the third embodiment.
Figure 38:
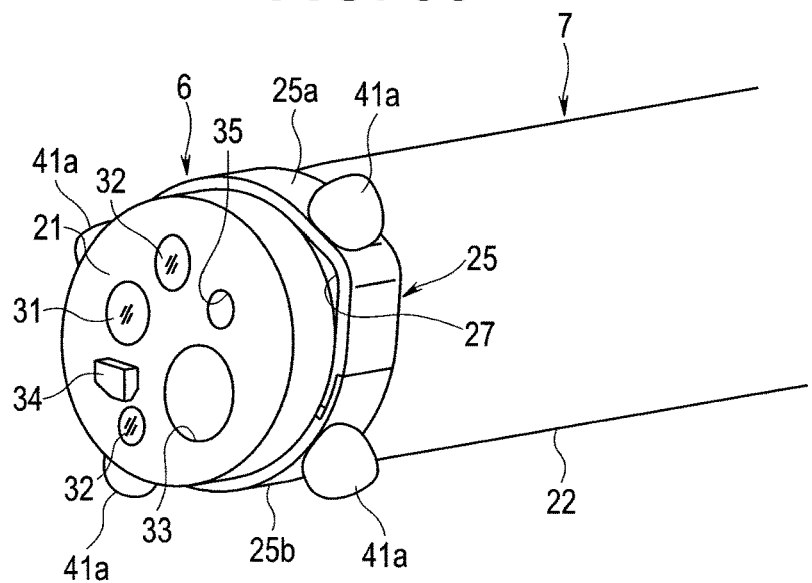
FIG. 38 is a perspective view illustrating a configuration of the distal end portion of the insertion portion of the second modification of the third embodiment on which a distal-end-side cover member is mounted.
Figure 39:
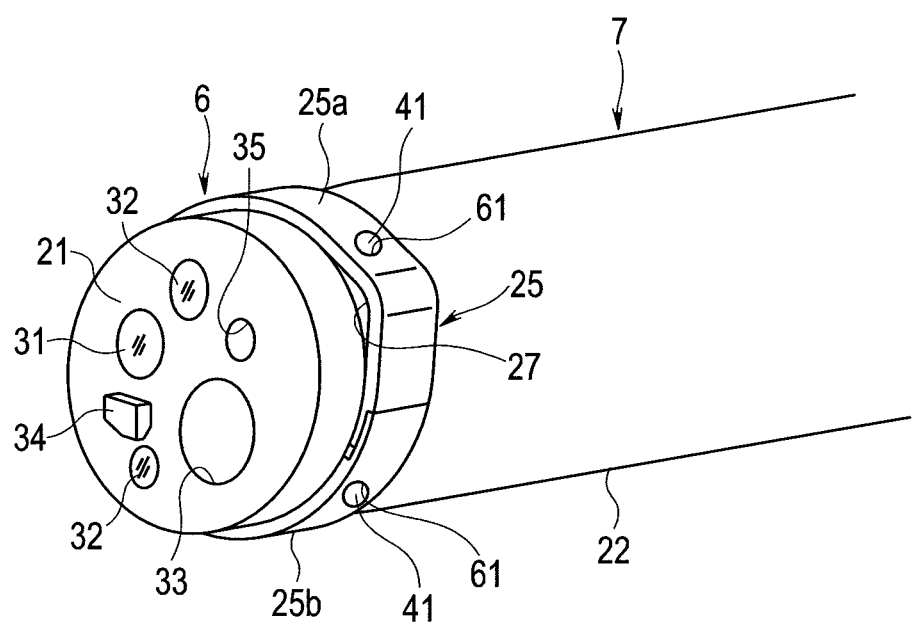
FIG. 39 is a perspective view of the distal end portion of the insertion portion of the second modification of the third embodiment illustrating a state in which an excess adhesive agent has been wiped off.

A plurality of hole portions 61, that is, two hole portions 61 here may be formed in each of the first-distal-end-side cover member 25a and the second distal-end-side cover member 25b of the distal-end-side cover member 25 as illustrated in FIG. 37, and the adhesive agent 41 of the spool adhesion portion 40 may be discharged from the four hole portions 61 as the excess adhesive agent 41a as illustrated in FIG. 38. As illustrated in FIG. 39, the excess adhesive agent 41a discharged from the four hole portions 61 is wiped off by the waste cloth 100 and the like.

Only the distal-end-side cover member 25 is exemplified here, but it goes without saying that the plurality of hole portions 61 may be formed in the first proximal-end-side cover member 26a and the second proximal-end-side cover member 26b of the proximal-end-side cover member 26.

(Third Modification)

Figure 40:
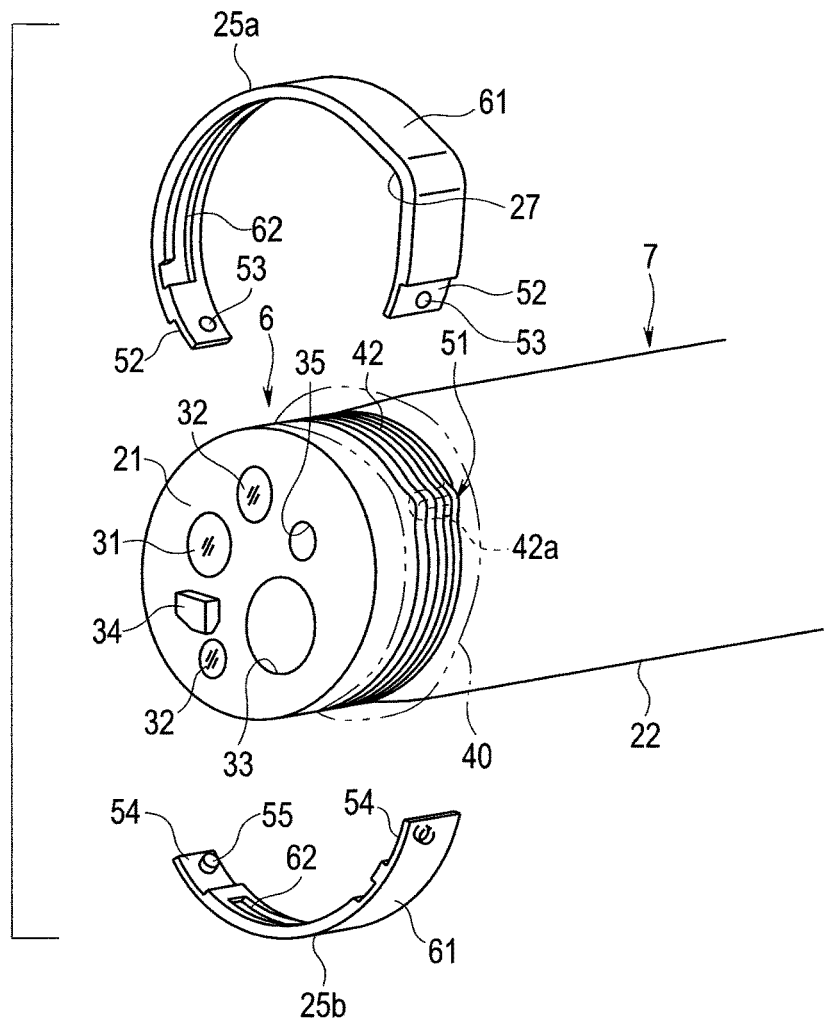
FIG. 40 is an exploded perspective view illustrating a configuration of a distal end portion of an insertion portion of a third modification of the third embodiment.
Figure 41:
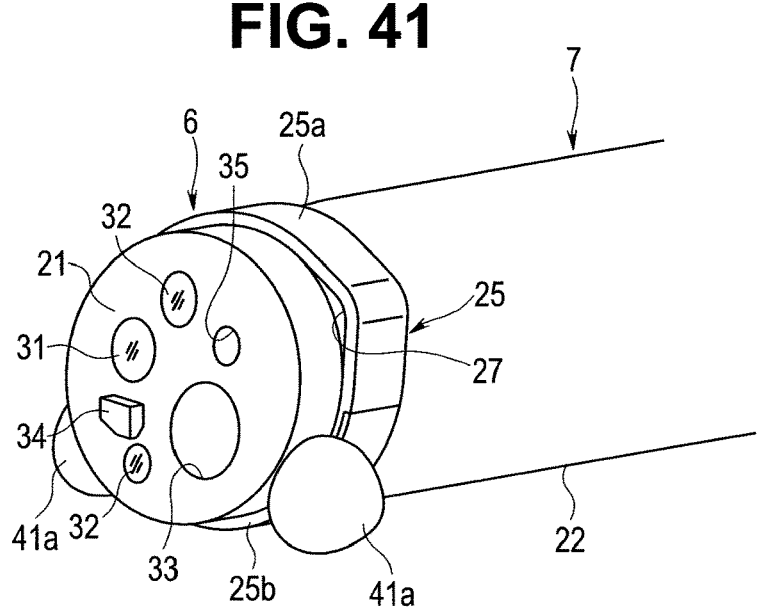
FIG. 41 is a perspective view illustrating a configuration of the distal end portion of the insertion portion of the third modification of the third embodiment on which a distal-end-side cover member is mounted.

An L-shaped groove portion 62 opened in an end portion on the distal end side may be formed on an inner surface side of each of the first-distal-end-side cover member 25a and the second distal-end-side cover member 25b of the distal-end-side cover member 25 as illustrated in FIG. 40, and the adhesive agent 41 of the spool adhesion portion 40 may be discharged from the openings of the groove portions 62 as the excess adhesive agent 41a as illustrated in FIG. 41.

In other words, by providing the groove portions 62 in the inner circumferential surfaces of the first-distal-end-side cover member 25a and the second distal-end-side cover member 25b, the adhesive agent 41a that oozes out is guided such that an appropriate amount of the adhesive agent remains on adhesion surfaces when the distal-end-side cover member 25 is correctly disposed.

Figure 42:
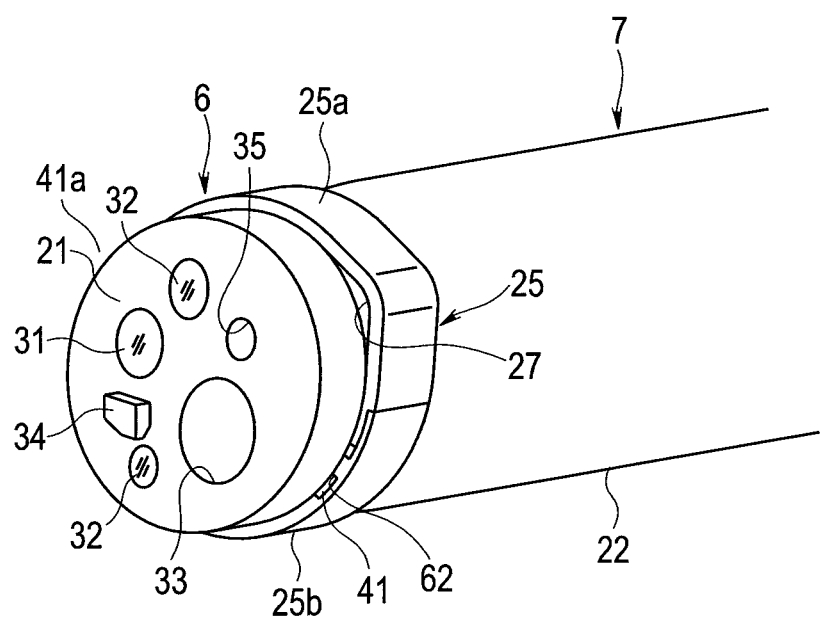
FIG. 42 is a perspective view of the distal end portion of the insertion portion of the third modification of the third embodiment illustrating a state in which an excess adhesive agent has been wiped off.

As illustrated in FIG. 42, the excess adhesive agent 41a discharged from the openings of the groove portions 62 is wiped off by the waste cloth 100 and the like.

Only the distal-end-side cover member 25 is exemplified here, but it goes without saying that the groove portions 62 may be formed so as to be opened in end portions from inner surfaces of the first proximal-end-side cover member 26a and the second proximal-end-side cover member 26b of the proximal-end-side cover member 26.

(Fourth Modification)

Figure 43:
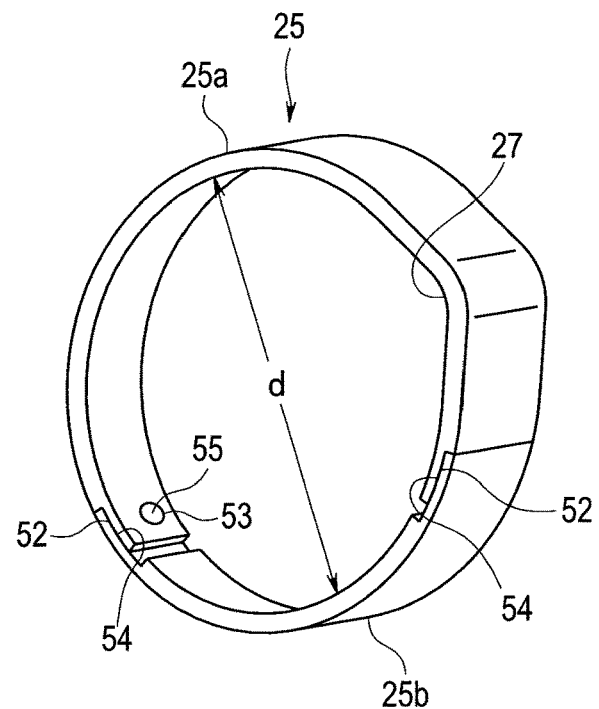
FIG. 43 is a perspective view illustrating a configuration of a distal-end-side cover member of a fourth modification of the third embodiment.
Figure 44:
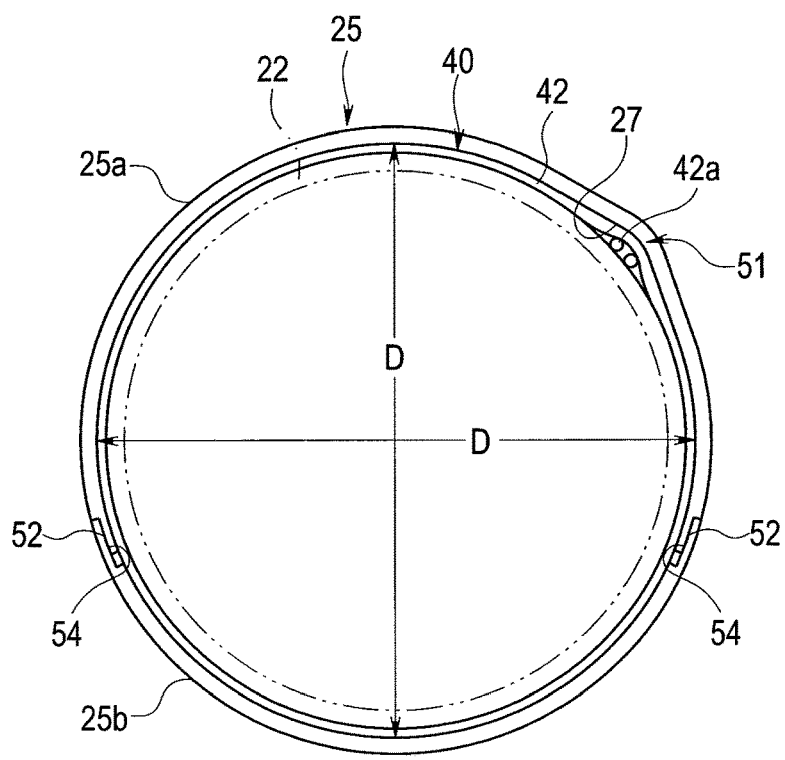
FIG. 44 is a view illustrating a state of the fourth modification of the third embodiment in which a distal-end-side cover member is mounted on a spool adhesion portion.

In the distal-end-side cover member 25, an inner diameter d in a state in which the first-distal-end-side cover member 25a and the second distal-end-side cover member 25b are coupled to each other as illustrated in FIG. 43 may be set to be smaller (d<D) than a predetermined outer diameter D of a spool portion in which the filamentous member 42 of the spool adhesion portion 40 is wound as illustrated in FIG. 44.

As a result, an inner surface of the distal-end-side cover member 25 presses the spool portion in the radially inward direction in a state in which the first-distal-end-side cover member 25a and the second distal-end-side cover member 25b are coupled to each other and are mounted on the spool adhesion portion 40, and hence the distal-end-side cover member 25 is placed in a state of being held without rotating and not moving in the front-rear direction even when the restricting concave portion 27 is not in a state of being shifted from the restricting convex portion 51 in the circumferential direction.

Only the distal-end-side cover member 25 is exemplified here, but the proximal-end-side cover member 26 may have a similar configuration.

(Fifth Modification)

Figure 45:
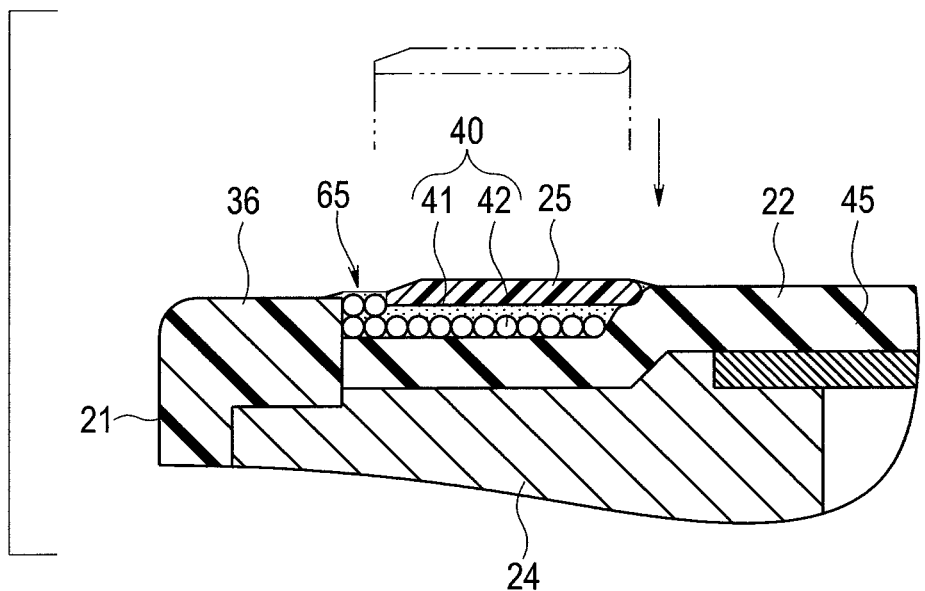
FIG. 45 is a partial cross-sectional view of a part of a fifth modification of the third embodiment on which a distal-end-side cover member is mounted and a restricting convex portion is provided.
Figure 46:
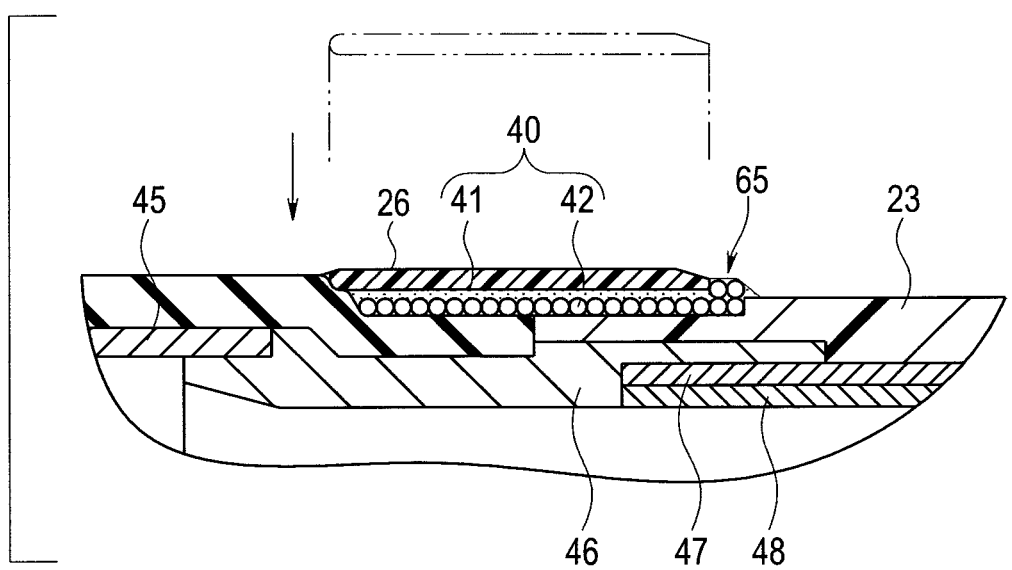
FIG. 46 is a partial cross-sectional view of a part of the fifth modification of the third embodiment on which a proximal-end-side cover member is mounted and the restricting convex portion is provided.

When each of the distal-end-side cover member 25 and the proximal-end-side cover member 26 is caused to have a two-body structure as described above, the filamentous members 42 of the spool adhesion portions 40 may be double wound and caused to be restricting convex portions 65 that protrude about the outer circumference as illustrated in FIG. 45 and FIG. 46.

The invention described in the embodiments and the modifications above is not limited to those embodiments and modifications, and it is possible to enable various modifications to be made besides the above without departing from the gist of the invention in the implementation phase. The embodiments and the modifications above include the invention in various phases, and various inventions may be extracted by appropriate combinations of a plurality of components that are disclosed.

For example, even when some components are erased from all of the components described in the embodiments and the modifications, a configuration from which those components are erased may be extracted as the invention when the described problem to be solved can be solved and the described effect may be obtained.

What is claimed is:

1. An endoscope comprising:
   an insertion portion comprising:
      a filament wound around an outer surface of a longitudinal portion of the insertion portion;
      a resin covering the filament; and
      a cover mounted on an outer surface of the resin, the cover comprising a concave portion provided on an inner circumferential surface of the cover;
   wherein the insertion portion comprising a protrusion protruding radially outward from a partial circumferential portion of an outer circumferential surface of the insertion portion; and
   the concave portion is disposed in a position shifted from the protrusion in a circumferential direction of the insertion portion.

2. The endoscope according to claim 1, wherein the cover is positioned to cover the protrusion.

3. The endoscope according to claim 2, wherein the filament is stacked in a radial direction of the insertion portion to form the protrusion.

4. The endoscope according to claim 1, wherein the resin includes an adhesive agent that fixes the filament to the insertion portion and fixes the cover to the insertion portion.

5. The endoscope according to claim 1, wherein:
   the filament includes a first filament and a second filament, the first filament is wound around one end of a bending portion skin that covers a bending portion of the insertion portion, the second filament is wound around an other end of the bending portion skin;
   an outer diameter of the bending portion skin where the filament is wound is smaller than an other portion of the bending portion.

6. The endoscope according to claim 5, wherein the cover is between the protrusion and the other portion of the bending portion skin in a longitudinal direction of the insertion portion.

7. The endoscope according to claim 5, wherein the cover includes a first cover and a second cover, the first cover covers the first filament, the second cover covers the second filament.

8. The endoscope according to claim 1, wherein the cover is a ring.

9. The endoscope according to claim 8, wherein the ring comprises two arc-shaped members having respective end portions coupled to each other.

10. The endoscope according to claim 1, wherein a cross section shape of the protrusion is similar to a cross sectional shape of the concave portion.

11. The endoscope according to claim 1, wherein the protrusion further extends in a longitudinal direction of the insertion portion.

12. The endoscope according to claim 1, wherein the cover further includes a hole penetrating from an outer circumferential surface to the inner circumferential surface.

13. The endoscope according to claim 1, wherein the cover further includes a groove on the inner circumferential surface of the cover, the groove is opened to an outside of the cover.

14. The endoscope according to claim 1, wherein, when the cover covers a portion of the outer circumferential surface of the insertion portion adjacent to the protrusion, an edge of the cover abuts the protrusion.

15. The endoscope according to claim 14, wherein the cover further includes a first mark aligned with a second mark on the outer circumferential surface of the insertion portion to position the cover at a position where the concave portion is shifted from the protrusion.

16. The endoscope according to claim 14, wherein the cover further includes a stopper projecting longitudinally towards the protrusion and circumferentially offset from the protrusion.

17. The endoscope according to claim 1, wherein the concave portion is fixed both longitudinally and circumferentially relative to the insertion section.

18. The endoscope according to claim 1, wherein the concave portion is fixed in the position shifted from the protrusion in the circumferential direction of the insertion portion.

19. An endoscope comprising:
an insertion portion comprising:
a filament wound around an outer surface of a longitudinal portion of the insertion portion;
a resin covering the filament; and
a cover mounted on an outer surface of the resin, the cover comprising a protrusion provided on an inner circumferential surface of the cover;
wherein the insertion portion comprising a concave portion provided at a partial circumferential portion of an outer circumferential surface of the outer surface of the insertion portion; and
the protrusion is disposed in a position shifted from the concave portion in a circumferential direction of the insertion portion.

20. A method for manufacturing an endoscope, comprising:
providing a skin on an outer surface of an insertion portion configured to be inserted into a subject;
winding a filament around an outer surface of an end portion of the skin and causing the end portion of the skin to be fixed to the insertion portion;
applying a resin to the filament wound around the skin;
passing a cover having a concave portion over a protrusion protruding radially outward from a partial circumferential portion of an outer circumferential surface of the insertion portion to cover the resin;
rotating the cover at predetermined angle to a position shifted from the protrusion in a circumferential direction of the insertion portion to sandwich the cover between the skin and the protrusion; and
wiping off an excess of the resin that oozes out from an end portion of the cover.

* * * * *